US009334330B2

(12) United States Patent
Birkle et al.

(10) Patent No.: US 9,334,330 B2
(45) Date of Patent: *May 10, 2016

(54) USE OF MONOCLONAL ANTIBODIES SPECIFIC TO THE O-ACETYLATED FORM OF GD2 GANGLIOSIDE FOR THE TREATMENT OF CERTAIN CANCERS

(71) Applicant: UNIVERSITE DE NANTES, Nantes (FR)

(72) Inventors: Stephane Birkle, Nantes (FR); Jean-Marie Mussini, Nantes (FR); Jacques Aubry, Nantes (FR); Jacques Barbet, Nantes (FR); Jean-Francois Chatal, Pornichet (FR); Beatrice Clemenceau, Nantes (FR)

(73) Assignee: UNIVERSITE DE NANTES, Nantes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/581,048

(22) Filed: Dec. 23, 2014

(65) Prior Publication Data

US 2015/0140023 A1 May 21, 2015

Related U.S. Application Data

(63) Continuation of application No. 12/445,071, filed as application No. PCT/EP2007/060750 on Oct. 10, 2007, now Pat. No. 8,951,524.

(30) Foreign Application Priority Data

Oct. 10, 2006 (FR) ........................................ 0608881

(51) Int. Cl.
*C07K 16/30* (2006.01)
*A61K 39/00* (2006.01)

(52) U.S. Cl.
CPC ....... *C07K 16/3084* (2013.01); *A61K 2039/505* (2013.01); *C07K 2317/24* (2013.01); *C07K 2317/622* (2013.01); *C07K 2317/73* (2013.01)

(58) Field of Classification Search
CPC .................. C07K 16/3084; C07K 2317/622; C07K 2317/24
USPC ..................................................... 424/183.1
See application file for complete search history.

(56) References Cited

U.S. PATENT DOCUMENTS 8,951,524 B2 * 2/2015 Birkle ................ C07K 16/3084
424/155.1

OTHER PUBLICATIONS

Cerato E, et al. (Hybridoma. Aug. 1997;16(4):307-16; abstract only).*

Alvarez-Rueda N, et al. (PLoS One. 2011;6(9):e25220. doi: 10.1371/journal.pone.0025220. Epub Sep. 22, 2011.*
Cochonneau D, et al. (Cancer Lett. Jun. 10, 2013;333(2):194-204. doi: 10.1016/j.canlet.2013.01.032. Epub Jan. 28, 2013).*
Terme M, et al., (PLoS One. Feb. 10, 2014;9(2):e87210. doi: 10.1371/journal.pone.0087210. eCollection 2014. Erratum in: PLoS One. 2014;9(7):e103395).*
ATCC Search Output for "8B6" Hybridoma (p. 1; Dec. 15, 2011).
Voskoglou-Nomikos (Clin. Can. Res. 9:4227-4239 (2003).
Dennis (Nature 442:739-741 (2006)).
Cespdes et al. (Clin. Trans. Oncol. 8(5):318-329 (2006)).
Talmadge et al. (Am. J. Pathol 170(3):793-804 (2007)).
Fujimori et al. (J. Nuc. Med. 31:1191-1198 (1990)).
Beckman et al. (Can. 109:170-179 (2007)).
Thurber et al. (Adv. Drug Deliv. Rev. 60:1421-1434 (2008)).
Rudnick et al. (Can. Biotherp. & Radiopharm. 24: 155-162 (2009)).
On-Line "Free Dicitonary Definition of Adjunction" (pp. 1-2; Dec. 15, 2011).
Aubry, J.; "Monoclonal Antibodies, 60C3 Anti-GD2 Ganglioside and Its O-Acetylated Form, "Hybridoma, 1997, vol. 16, No. 6, Abstract, 1 Page.
Aubry, J.; "Monoclonal Antibodies, 8B6 Anti-O-Acetyl GD2 "Hybridoma, 1997, vol. 16, No. 6, Abstract, 1 Page.
Cerato, et al., "Variable Region Gene Segments of Nine Monoclonal Antibodies Specific to Disialogangliosides (GD21 GD3) and Their O-Acetylated Derivatives, "Hybridoma, 1997, vol. 16, No. 4, pp. 307-316.
Chapman, P.B. et al, "Homophilic Binding of Mouse Monoclonal Antibodies Against GD3 Ganglioside," The Journal of Immunology, Aug. 1, 1990, vol. 145, No. 3, pp. 891-898.
Hamilton, W.B, et al., "Ganglioside Expression on Human Malignant Melanoma Assessed by Quantitative Immune Thin-Layer Chromatography, "Int. J. Cancer, 1993, vol. 53, pp. 566-573.
Mezazigh, A. et al.; "A Monoclonal Antibody Reacting Specifically for Ganglioside O-Acetylated Gd2 in Neuroectodermal Tumors,"Glycoconjugate Journal, Aug. 20, 1993, vol. 10, No. 4; pp. 300-301.
Sjoberg, E.R. et al.; "Structuaral an Immunological Characterization of O-Acetylated Gd21 Evidence That Gd2 is an Acceptor for Ganglioside O-Acetyltransferase in Human Melanoma Cells,"The Journal of Biological Chemistry, Aug. 15, 1992, vol. 267, No. 23, pp. 16200-16211.
Yan, L. et al.; Pharmacogenetics and Pharmacogenomics in Oncology Therapeutic Antibody Development, Bio Techniques, Oct. 2005, vol. 39; pp. 565-568.
Ye, J.N. et al; Alteration of Ganglioside Composition by Stable Transfection with Antisense Vectors against GD3-Synthase Gene Expression, Biochemistry, 1999, vol. 38, No. 27, pp. 8762-8769.
Zhang, H. et al.; Antibodies Against GD2 Ganglioside Can Eradicate Syngeneic Cancer Micrometastases, Cancer Research, Jul. 1, 1998, vol. 58; pp. 2844-2849.

* cited by examiner

*Primary Examiner* — Lynn Bristol
(74) *Attorney, Agent, or Firm* — Young & Thompson

(57) ABSTRACT

The monoclonal antibodies that only recognize the O-acetylated form of the GD2 ganglioside, or fragments of the antibody, for the diagnosis and the treatment of cancers in which the cells express the O-acetylated GD2, the antibody or the fragment recognizing the O-acetylated GD2 molecules expressed by the tumoral cells and not recognizing the GD2 molecules expressed at the surface of the peripheral nerves, in order to increase the specificity of the diagnosis and reduce the toxicity of the treatments. Also artificially modified antibodies advantageously used for treating and diagnosing cancers in which the cells express the O-acetylated GD2.

8 Claims, 15 Drawing Sheets

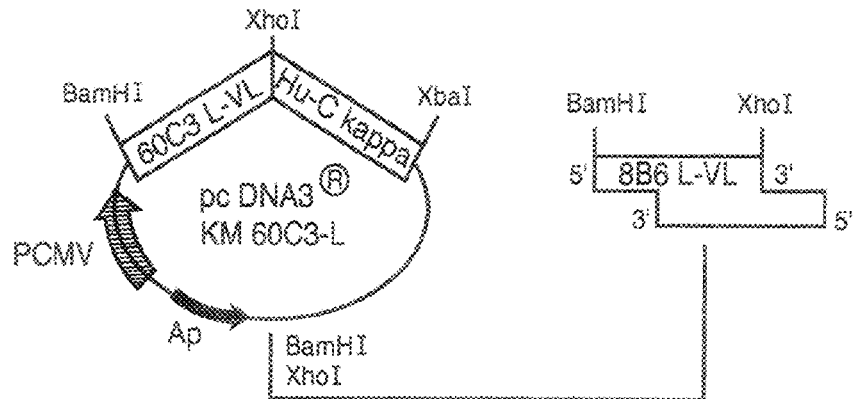
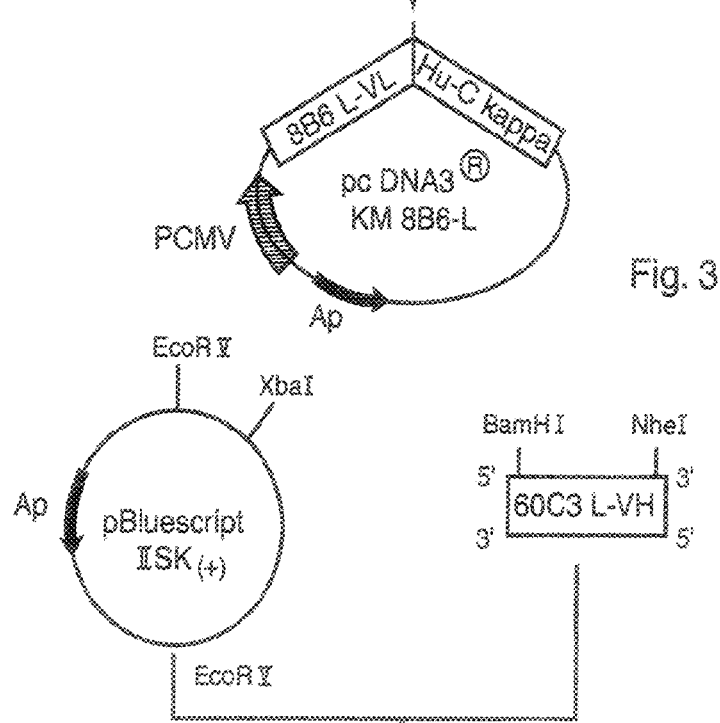
Fig. 3
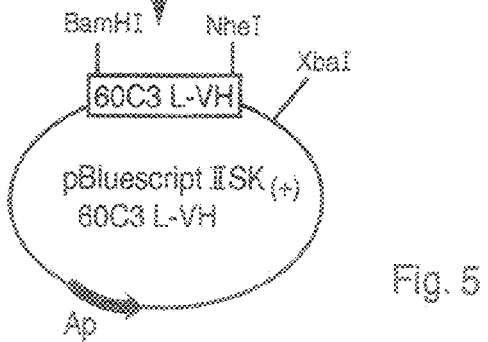
Fig. 5

|  | Concentration | | | |
| --- | --- | --- | --- | --- |
|  | 0 µg/mL | 0.1 µg/mL | 1 µg/mL | 10 µg/mL |
| 8B6 | 0% | 10% | 20% | 30% |
| KM8B6 | 0% | 16% | 23% | 44 |
| Non-specific mAb | 0% | 0% | 0% | 0% |

B

MKLWLNWIFLVTLLNGFQCEVKLVESGGGLVLPGDSLRLSCATSEFTFTDYYMTWVRQPPRKAL
←——— Ig kappa signal peptide ———>|<---------------------------------------------------------------

EWLGFIRNRANGYTTEYNPSVKGRFTISRDNSQSILYLQMNTLRTEDSATYYCARVSNWAFDYW
--------------------------------------- 8B6 VH ---------------------------------------

GQGTTLTVSSGGGGSGGGGSGGGGSDVVMTQTPLSLPVSLGDQASISCRSSQSLLKNNGNTFL
----------------------->|<------ (G4S)3 linker -----> |-------------------------------------

HWYLQKSGQSPKLLIYKVSNRLSGVPDRFSGSGSGTYFTLKISRVEAEDLGVYFCSQSTHIPYTFGG
------------------------ 8B6 VL ------------------------

GTKLEIKVECPPCPAPPVAGPSVFLFPPKPKDTLMISRTPEVTCVVVDVSHEDPEVKFNWYVDGV
----------->|<-----------------------------------------------------------------------------

EVHNAKTKPREEQYNSTYRVVSVLTVLHQDWLNGKEYKCKVSNKGLPSSIEKTISKAKGQPREPQ
---------------------------- Human engineered IgG1 Fc region ----------------------------

VYTLPPSREEMTKNQVSLTCLVKGFYPSDIAVEWESNGQPENNYKTTPPVLDSDGSFFLYSKLTV

DKSRWQQGNVFSCSVMHEALHNHYTQKSLSLSPGKPFWVLVVVGGVLACYSLLVTVAFIIFWV
-----------------------------------------------------------------------------------------→|<-----------

RSKRSRLLHSDYMNMTPRRPGPTRKHYQPYAPPRDFAAYRSRVKFSRSADAPAYQQGQNQLYNE
-------------- CD28 -----------------------------------------------------→|<---------

LNLGRREEYDVLDKRRGRDPEMGGKPQRRKNPQEGLYNELQKDKMAEAYSEIGMKGERRRGKG
---------------------------------- CD3 zeta ----------------------------------

HDGLYQGLSTATKDTYDALHMQALPPR    SEQ ID NO: 35

FIGURE 17

SEQUENCE LISTING

<160> NUMBER OF SEQ ID NOS: 41

<210> SEQ ID NO 1
<211> LENGTH: 137
<212> TYPE: PRT
<213> ORGANISM: Mus musculus

<400> SEQUENCE: 1

Met Lys Leu Trp Leu Asn Trp Ile Phe Leu Val Thr Leu Leu Asn Gly
1               5                   10                  15

Phe Gln Cys Glu Val Lys Leu Val Glu Ser Gly Gly Gly Leu Val Leu
            20                  25                  30

Pro Gly Asp Ser Leu Arg Leu Ser Cys Ala Thr Ser Glu Phe Thr Phe
        35                  40                  45

Thr Asp Tyr Tyr Met Thr Trp Val Arg Gln Pro Pro Arg Lys Ala Leu
    50                  55                  60

Glu Trp Leu Gly Phe Ile Arg Asn Arg Ala Asn Gly Tyr Thr Thr Glu
65                  70                  75                  80

Tyr Asn Pro Ser Val Lys Gly Arg Phe Thr Ile Ser Arg Asp Asn Ser
                85                  90                  95

Gln Ile Leu Tyr Leu Gln Met Asn Thr Leu Arg Thr Glu Asp Ser Ala
            100                 105                 110

Thr Tyr Tyr Cys Ala Arg Val Ser Asn Trp Ala Phe Asp Tyr Trp Gly
        115                 120                 125

Gln Thr Thr Leu Thr Val Ser Ser Ala
    130                 135

<210> SEQ ID NO 2
<211> LENGTH: 8
<212> TYPE: PRT
<213> ORGANISM: Mus musculus

<400> SEQUENCE: 2

Glu Phe Thr Phe Thr Asp Tyr Tyr
1               5

<210> SEQ ID NO 3
<211> LENGTH: 10
<212> TYPE: PRT
<213> ORGANISM: Mus musculus

```
<400> SEQUENCE: 3

Ile Arg Asn Arg Ala Asn Gly Tyr Thr Thr
1               5                   10

<210> SEQ ID NO 4
<211> LENGTH: 10
<212> TYPE: PRT
<213> ORGANISM: Mus musculus

<400> SEQUENCE: 4

Ala Arg Val Ser Asn Trp Ala Phe Asp Tyr
1               5                   10

<210> SEQ ID NO 5
<211> LENGTH: 133
<212> TYPE: PRT
<213> ORGANISM: Mus musculus

<400> SEQUENCE: 5

Met Lys Leu Pro Val Arg Leu Leu Val Leu Met Phe Trp Ile Pro Gly
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Leu Lys Asn Asn Gly Asn Thr Phe Leu His Trp Tyr Leu Gln Lys Ser
    50                  55                  60

Gly Gln Ser Pro Lys Leu Leu Ile Tyr Lys Val Ser Asn Arg Leu Ser
65                  70                  75                  80

Gly Val Pro Asp Arg Phe Ser Gly Ser Gly Ser Gly Thr Tyr Phe Thr
                85                  90                  95

Leu Lys Ile Ser Arg Val Glu Ala Glu Asp Leu Gly Val Tyr Phe Cys
            100                 105                 110

Ser Gln Ser Thr His Ile Pro Tyr Thr Phe Gly Gly Gly Thr Lys Leu
        115                 120                 125

Glu Leu Lys Arg Thr
    130

<210> SEQ ID NO 6
<211> LENGTH: 12
<212> TYPE: PRT
<213> ORGANISM: Mus musculus

<400> SEQUENCE: 6

Gln Ser Leu Leu Lys Asn Asn Gly Asn Thr Phe Leu
1               5                   10

<210> SEQ ID NO 7
<211> LENGTH: 3
<212> TYPE: PRT
<213> ORGANISM: Mus musculus

<400> SEQUENCE: 7

Lys Val Ser
1

<210> SEQ ID NO 8
<211> LENGTH: 9
<212> TYPE: PRT
<213> ORGANISM: Mus musculus
```

```
<400> SEQUENCE: 8

Ser Gln Ser Thr His Ile Pro Tyr Thr
1               5

<210> SEQ ID NO 9
<211> LENGTH: 24
<212> TYPE: DNA
<213> ORGANISM: Artificial sequence
<220> FEATURE:
<223> OTHER INFORMATION: antisense primer specific of 60C3 VL

<400> SEQUENCE: 9
tttcagctcc agcttggtcc cagc                                          24

<210> SEQ ID NO 10
<211> LENGTH: 23
<212> TYPE: DNA
<213> ORGANISM: Artificial sequence
<220> FEATURE:
<223> OTHER INFORMATION: sense primer specific of 60C3 L-VL

<400> SEQUENCE: 10
agggatccaa agacaaaatg gat                                           23

<210> SEQ ID NO 11
<211> LENGTH: 26
<212> TYPE: DNA
<213> ORGANISM: Artificial sequence
<220> FEATURE:
<223> OTHER INFORMATION: antisense primer specific of 60C3 L-VL

<400> SEQUENCE: 11
ttcagctcga gcttggtccc agcacc                                        26

<210> SEQ ID NO 12
<211> LENGTH: 30
<212> TYPE: DNA
<213> ORGANISM: Artificial sequence
<220> FEATURE:
<223> OTHER INFORMATION: sense primer specific of 60C3L-VL

<400> SEQUENCE: 12
agctcgagct gaaacgaact gtggctgcac                                    30

<210> SEQ ID NO 13
<211> LENGTH: 29
<212> TYPE: DNA
<213> ORGANISM: Artificial sequence
<220> FEATURE:
<223> OTHER INFORMATION: antisense primer specific of 60C3L-VL

<400> SEQUENCE: 13
cttctagatt taacactctc ccctgttga                                     29

<210> SEQ ID NO 14
<211> LENGTH: 30
<212> TYPE: DNA
<213> ORGANISM: Artificial sequence
<220> FEATURE:
<223> OTHER INFORMATION: sens primer of 8B6 L-VL

<400> SEQUENCE: 14
aagggatccg ccaccatgaa gttgcctgtt                                    30

<210> SEQ ID NO 15
```

```
<211> LENGTH: 24
<212> TYPE: DNA
<213> ORGANISM: Artificial sequence
<220> FEATURE:
<223> OTHER INFORMATION: antisens primer of 8B6 L-VL

<400> SEQUENCE: 15
ccgttttatc tcgagcttgg tccc                                              24

<210> SEQ ID NO 16
<211> LENGTH: 30
<212> TYPE: DNA
<213> ORGANISM: Artificial sequence
<220> FEATURE:
<223> OTHER INFORMATION: antisens primer specific of 60C3 L-VH

<400> SEQUENCE: 16
tgcagagaca gtgaccagca gagtagtccc                                        30

<210> SEQ ID NO 17
<211> LENGTH: 31
<212> TYPE: DNA
<213> ORGANISM: Artificial sequence
<220> FEATURE:
<223> OTHER INFORMATION: sense primer specific of 60C3 L-VH

<400> SEQUENCE: 17
caggatccga acacactgac tctaaccatg g                                      31

<210> SEQ ID NO 18
<211> LENGTH: 28
<212> TYPE: DNA
<213> ORGANISM: Artificial sequence
<220> FEATURE:
<223> OTHER INFORMATION: antisense primer specific of 60C3 L-VH

<400> SEQUENCE: 18
tgctagctgc agagacagtg accagagt                                          28

<210> SEQ ID NO 19
<211> LENGTH: 30
<212> TYPE: DNA
<213> ORGANISM: Artificial sequence
<220> FEATURE:
<223> OTHER INFORMATION: sens primer specific of hu-C gamma 1

<400> SEQUENCE: 19
cagctagcac caagggccca tcggtcttcc                                        30

<210> SEQ ID NO 20
<211> LENGTH: 35
<212> TYPE: DNA
<213> ORGANISM: Artificial sequence
<220> FEATURE:
<223> OTHER INFORMATION: antisens primer specific of hu-C gamma 1

<400> SEQUENCE: 20
agcctctccc tgtctccggg taaataatct agacg                                  35

<210> SEQ ID NO 21
<211> LENGTH: 31
<212> TYPE: DNA
<213> ORGANISM: Artificial sequence
<220> FEATURE:
<223> OTHER INFORMATION: sens primer BAmHI 60C3 L-VH

<400> SEQUENCE: 21
```
caggatccga acacactgac tctaaccatg g                                    31

<210> SEQ ID NO 22
<211> LENGTH: 35
<212> TYPE: DNA
<213> ORGANISM: Artificial sequence
<220> FEATURE:
<223> OTHER INFORMATION: antisens primer BAmHI 60C3 L-VH

<400> SEQUENCE: 22
agcctctccc tgtctccggg taaataatct agacg                                35

<210> SEQ ID NO 23
<211> LENGTH: 29
<212> TYPE: DNA
<213> ORGANISM: Artificial sequence
<220> FEATURE:
<223> OTHER INFORMATION: antisense probe specific to the 8B6 L-VH cDNA

<400> SEQUENCE: 23
gatcaactca gtcttgctgg ctgggtggg                                       29

<210> SEQ ID NO 24
<211> LENGTH: 30
<212> TYPE: DNA
<213> ORGANISM: Artificial sequence
<220> FEATURE:
<223> OTHER INFORMATION: sens primer BamHI 8B6 L-VH

<400> SEQUENCE: 24
ccgtcggatc cggccaccat gaagttgtgg                                      30

<210> SEQ ID NO 25
<211> LENGTH: 24
<212> TYPE: DNA
<213> ORGANISM: Artificial sequence
<220> FEATURE:
<223> OTHER INFORMATION: antisens primer NheI 8B6 L-VH

<400> SEQUENCE: 25
cggggtgcta gctgaggaga ctgt                                            24

<210> SEQ ID NO 26
<211> LENGTH: 30
<212> TYPE: DNA
<213> ORGANISM: Artificial sequence
<220> FEATURE:
<223> OTHER INFORMATION: sens primer BamHI 60C3 L-VH

<400> SEQUENCE: 26
ccgtcggatc cggccaccat gaagttgtgg                                      30

<210> SEQ ID NO 27
<211> LENGTH: 24
<212> TYPE: DNA
<213> ORGANISM: Artificial sequence
<220> FEATURE:
<223> OTHER INFORMATION: antisense primer NheI 8B6 L-VH

<400> SEQUENCE: 27
cggggtgcta gctgaggaga ctgt                                            24

<210> SEQ ID NO 28
<211> LENGTH: 19
<212> TYPE: PRT

<213> ORGANISM: Homo sapiens

<400> SEQUENCE: 28

Met Lys Leu Trp Leu Asn Trp Ile Phe Leu Val Thr Leu Leu Asn Gly
1               5                   10                  15

Phe Gln Cys

<210> SEQ ID NO 29
<211> LENGTH: 47
<212> TYPE: PRT
<213> ORGANISM: Mus musculus

<400> SEQUENCE: 29

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp
        35                  40                  45

<210> SEQ ID NO 30
<211> LENGTH: 15
<212> TYPE: PRT
<213> ORGANISM: Artificial sequence
<220> FEATURE:
<223> OTHER INFORMATION: flexible linker

<400> SEQUENCE: 30

Gly Gly Gly Gly Ser Gly Gly Gly Gly Ser Gly Gly Gly Gly Ser
1               5                   10                  15

<210> SEQ ID NO 31
<211> LENGTH: 112
<212> TYPE: PRT
<213> ORGANISM: Mus musculus

<400> SEQUENCE: 31

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 32
<211> LENGTH: 223
<212> TYPE: PRT
<213> ORGANISM: Homo sapiens

<400> SEQUENCE: 32

Val Glu Cys Pro Pro Cys Pro Ala Pro Pro Val Ala Gly Pro Ser Val
1               5                   10                  15

```
Phe Leu Phe Pro Pro Lys Pro Lys Asp Thr Leu Met Ile Ser Arg Thr
             20                  25                  30

Pro Glu Val Thr Cys Val Val Val Asp Val Ser His Glu Asp Pro Glu
         35                  40                  45

Val Lys Phe Asn Trp Tyr Val Asp Gly Val Glu Val His Asn Ala Lys
 50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                 85                  90                  95

Cys Lys Val Ser Asn Lys Gly Leu Pro Ser Ser Ile Glu Lys Thr Ile
                100                 105                 110

Ser Lys Ala Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
        210                 215                 220

<210> SEQ ID NO 33
<211> LENGTH: 69
<212> TYPE: PRT
<213> ORGANISM: Homo sapiens

<400> SEQUENCE: 33

Pro Phe Trp Val Leu Val Val Val Gly Gly Val Leu Ala Cys Tyr Ser
1               5                   10                  15

Leu Leu Val Thr Val Ala Phe Ile Ile Phe Trp Val Arg Ser Lys Arg
            20                  25                  30

Ser Arg Leu Leu His Ser Asp Tyr Met Asn Met Thr Pro Arg Arg Pro
        35                  40                  45

Gly Pro Thr Arg Lys His Tyr Gln Pro Tyr Ala Pro Pro Arg Asp Phe
    50                  55                  60

Ala Ala Tyr Arg Ser
65

<210> SEQ ID NO 34
<211> LENGTH: 113
<212> TYPE: PRT
<213> ORGANISM: Homo sapiens

<400> SEQUENCE: 34

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45
```

Pro Gln Arg Arg Lys Asn Pro Gln Glu Gly Leu Tyr Asn Glu Leu Gln
            50                  55                  60

Lys Asp Lys Met Ala Glu Ala Tyr Ser Glu Ile Gly Met Lys Gly Glu
 65                  70                  75                  80

Arg Arg Arg Gly Lys Gly His Asp Gly Leu Tyr Gln Gly Leu Ser Thr
                 85                  90                  95

Ala Thr Lys Asp Thr Tyr Asp Ala Leu His Met Gln Ala Leu Pro Pro
            100                 105                 110

Arg

<210> SEQ ID NO 35
<211> LENGTH: 670
<212> TYPE: PRT
<213> ORGANISM: Artificial sequence
<220> FEATURE:
<223> OTHER INFORMATION: chimeric antigen receptor construct

<400> SEQUENCE: 35

Met Lys Leu Trp Leu Asn Trp Ile Phe Leu Val Thr Leu Leu Asn Gly
  1               5                  10                  15

Phe Gln Cys Glu Val Lys Leu Val Glu Ser Gly Gly Gly Leu Val Leu
                 20                  25                  30

Pro Gly Asp Ser Leu Arg Leu Ser Cys Ala Thr Ser Glu Phe Thr Phe
             35                  40                  45

Thr Asp Tyr Tyr Met Thr Trp Val Arg Gln Pro Pro Arg Lys Ala Leu
 50                  55                  60

Glu Trp Leu Gly Phe Ile Arg Asn Arg Ala Asn Gly Tyr Thr Thr Glu
 65                  70                  75                  80

Tyr Asn Pro Ser Val Lys Gly Arg Phe Thr Ile Ser Arg Asp Asn Ser
                 85                  90                  95

Gln Ser Ile Leu Tyr Leu Gln Met Asn Thr Leu Arg Thr Glu Asp Ser
            100                 105                 110

Ala Thr Tyr Tyr Cys Ala Arg Val Ser Asn Trp Ala Phe Asp Tyr Trp
            115                 120                 125

Gly Gln Gly Thr Thr Leu Thr Val Ser Ser Gly Gly Gly Gly Ser Gly
        130                 135                 140

Gly Gly Ser Gly Gly Gly Ser Asp Val Val Met Thr Gln Thr
145                 150                 155                 160

Pro Leu Ser Leu Pro Val Ser Leu Gly Asp Gln Ala Ser Ile Ser Cys
                165                 170                 175

Arg Ser Ser Gln Ser Leu Leu Lys Asn Asn Gly Asn Thr Phe Leu His
            180                 185                 190

Trp Tyr Leu Gln Lys Ser Gly Gln Ser Pro Lys Leu Leu Ile Tyr Lys
        195                 200                 205

Val Ser Asn Arg Leu Ser Gly Val Pro Asp Arg Phe Ser Gly Ser Gly
210                 215                 220

Ser Gly Thr Tyr Phe Thr Leu Lys Ile Ser Arg Val Glu Ala Glu Asp
225                 230                 235                 240

Leu Gly Val Tyr Phe Cys Ser Gln Ser Thr His Ile Pro Tyr Thr Phe
                245                 250                 255

Gly Gly Gly Thr Lys Leu Glu Ile Lys Val Glu Cys Pro Pro Cys Pro
            260                 265                 270

Ala Pro Pro Val Ala Gly Pro Ser Val Phe Leu Phe Pro Pro Lys Pro
        275                 280                 285

Lys Asp Thr Leu Met Ile Ser Arg Thr Pro Glu Val Thr Cys Val Val

```
            290                 295                 300
Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
                340                 345                 350

Asp Trp Leu Asn Gly Lys Glu Tyr Lys Cys Lys Val Ser Asn Lys Gly
            355                 360                 365

Leu Pro Ser Ser Ile Glu Lys Thr Ile Ser Lys Ala Lys Gly Gln Pro
370                 375                 380

Arg Glu Pro Gln Val Tyr Thr Leu Pro Pro Ser Arg Glu Glu Met Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
                420                 425                 430

Lys Thr Thr Pro Pro Val Leu Asp Ser Asp Gly Ser Phe Phe Leu Tyr
            435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Lys Pro Phe Trp Val Leu Val Val Val
                485                 490                 495

Gly Gly Val Leu Ala Cys Tyr Ser Leu Leu Val Thr Val Ala Phe Ile
            500                 505                 510

Ile Phe Trp Val Arg Ser Lys Arg Ser Arg Leu Leu His Ser Asp Tyr
            515                 520                 525

Met Asn Met Thr Pro Arg Arg Pro Gly Pro Thr Arg Lys His Tyr Gln
530                 535                 540

Pro Tyr Ala Pro Pro Arg Asp Phe Ala Ala Tyr Arg Ser Arg Val Lys
545                 550                 555                 560

Phe Ser Arg Ser Ala Asp Ala Pro Ala Tyr Gln Gln Gly Gln Asn Gln
                565                 570                 575

Leu Tyr Asn Glu Leu Asn Leu Gly Arg Arg Glu Glu Tyr Asp Val Leu
            580                 585                 590

Asp Lys Arg Arg Gly Arg Asp Pro Glu Met Gly Gly Lys Pro Gln Arg
            595                 600                 605

Arg Lys Asn Pro Gln Glu Gly Leu Tyr Asn Glu Leu Gln Lys Asp Lys
            610                 615                 620

Met Ala Glu Ala Tyr Ser Glu Ile Gly Met Lys Gly Glu Arg Arg Arg
625                 630                 635                 640

Gly Lys Gly His Asp Gly Leu Tyr Gln Gly Leu Ser Thr Ala Thr Lys
                645                 650                 655

Asp Thr Tyr Asp Ala Leu His Met Gln Ala Leu Pro Pro Arg
            660                 665                 670

<210> SEQ ID NO 36
<211> LENGTH: 733
<212> TYPE: DNA
<213> ORGANISM: Artificial Sequence
<220> FEATURE:
<223> OTHER INFORMATION: the nucleotide sequence and the amino
      acid-deduced sequence of the light chain of the artificially
``` modified antibody KM8B6

<400> SEQUENCE: 36

```
ggatccgcca ccatgaagtt ccctgttagg ctgttggtgc tgatgttctg gattcctggt      60
tccagcagtg atgtgtgatc acccaaactc cactctccct gcctgtcact cttggagatc     120
aagcctcaat ctcttgcaga tctagtcaga gccttctaaa aaataatgga acacctttt      180
tacattggta cctgcagaag tcaggccagt ctccaaagct ccttatctac aaagtttcca     240
accgactttc tggggtccca gacaggttca gtggcagtgg atcagggaca tatttcacac     300
tcaagatcag cagagtggag gctgaggatc tgggagttta tttctgctct caaagtacac     360
atattccgta cacattcgga gggggaccaa gctcgagctg aaacgaact gtggctgcac      420
catctgtctt catcttcccg ccatctgatg agcagttgaa atctggaact gcctctgttg     480
tgtgcctgct gattaacttc tatcccagga ggccaaagta cagtggaagg tggataacgc     540
cctccaatcg ggtaactccc aggagagtgt cacagagcag acagcaagg acagcaccta     600
cagcctcagc agcaccctga cgctgagcaa agcagactac gagaaacaca agtctacgc     660
ctgcgaagtc acccatcagg gcctgagctc gcccgtcaca aagagcttca cagcggaga     720
gtgttaatct aga                                                        733
```

<210> SEQ ID NO 37
<211> LENGTH: 1425
<212> TYPE: DNA
<213> ORGANISM: Artificial Sequence
<220> FEATURE:
<223> OTHER INFORMATION: the nucleotide sequence and the deduced amino
      acid sequence of the artificially modified antibody heavy chain
      KM8B6

<400> SEQUENCE: 37

```
ggatccggcc acatgaagtt gtggctgaac tggattttcc ttgtaacact tttaaatggt      60
tccagtgga ggtgaaactg gtggagtctg gaggaggctt ggtgctgcct ggggattctc     120
tgagactctc ctgtgcaact tctgagttca ccttcactga ttactacatg acttgggtcc     180
gccagcctcc aagaaaggca cttgagtggt tgggttttat tagaaacaga gctaatggtt     240
acacaacaga gtacaatcca tctgtgaagg gtcggttcac catttccaga gataaattcc     300
caaagcatcc tctatcttca atgaacaccc tgagaactg aggacagtgc acttattac      360
tgtgcaagag tctctaactg gcctttgac tactggggcc aaggcaccac tctcacagtc      420
tcctcagcta gcaccaaggg cccatcggtc ttccccctgg cacctcctc caagagcacc      480
tctgggggca gcggccct gggctgcctg gtcaaggact acttccccga accggtgacg     540
gtgtcgtgga actcaggcgc cctgaccagc ggcgtgcaca ccttcccggc tgtcctacag     600
tcctcaagac tctactccct cagcagcgtg gtgaccgtgc cctccagcag cttgggcacc     660
cagacctaca tctgcaacgt gaatcacaag cccagcaaca ccaaggtgga caagagagtt    720
gagcccaaat cttgtgacaa aactcacaca tgcccaccgt gcccagcacc tgaactcctg    780
ggggaccgt cagtcttcct cttcccccca aaacccaagg acaccctcat gatctcccgg     840
acccctgagg tcacatgcgt ggtggtggac gtgagccacg aagaccctga ggtcaagttc     900
aactggtacg tggacggcgt ggaggtgcat aatgccaaga caaagccgcg ggaggagcag     960
tacaacagca cgtaccgtgt ggtcagcgtc ctcaccgtcc tgcaccagga ctggctgaat    1020
ggcaaggagt acaagtgcaa ggtctccaac aaagccctcc cagcccccat cgagaaaacc    1080
atctccaaag ccaaagggca gccccgagaa ccacaggtgt acaccctgcc cccatcccgg    1140
```

```
gaggagatga ccaagaacca ggtcagcctg acctgcctgg tcaaaggctt ctatcccagc    1200
gacatcgccg tggagtggga gagcaatggg cagccggaga caactacaa gaccacgcct     1260 cccgtgctgg actccgacgg ctccttcttc ctctatagca agctcaccgt ggacaagagc    1320
aggtggcagc aggggaacgt cttctcatgc tccgtgatgc atgaggctct gcacaaccac    1380
tacacgcaga agagcctctc cctgtctccg ggtaaataat ctaga                    1425
```

```
<210> SEQ ID NO 38
<211> LENGTH: 5
<212> TYPE: PRT
<213> ORGANISM: Artificial Sequence
<220> FEATURE:
<223> OTHER INFORMATION: flexible linker GSGG(S)n
<220> FEATURE:
<221> NAME/KEY: REPEAT
<222> LOCATION: (5)..(5)
<223> OTHER INFORMATION: n is at least 1

<400> SEQUENCE: 38

Gly Ser Gly Gly Ser
1               5

<210> SEQ ID NO 39
<211> LENGTH: 4
<212> TYPE: PRT
<213> ORGANISM: Artificial Sequence
<220> FEATURE:
<223> OTHER INFORMATION: flexible linker GGG(S)n
<220> FEATURE:
<221> NAME/KEY: REPEAT
<222> LOCATION: (4)..(4)
<223> OTHER INFORMATION: n is at least 1

<400> SEQUENCE: 39

Gly Gly Gly Ser
1

<210> SEQ ID NO 40
<211> LENGTH: 5
<212> TYPE: PRT
<213> ORGANISM: Artificial Sequence
<220> FEATURE:
<223> OTHER INFORMATION: flexible linker GGGG(S)n
<220> FEATURE:
<221> NAME/KEY: REPEAT
<222> LOCATION: (5)..(5)
<223> OTHER INFORMATION: n is at least 1

<400> SEQUENCE: 40

Gly Gly Gly Gly Ser
1               5

<210> SEQ ID NO 41
<211> LENGTH: 4
<212> TYPE: PRT
<213> ORGANISM: Artificial Sequence
<220> FEATURE:
<223> OTHER INFORMATION: phosphoinositide 3-kinase (PI3K) binding motif
      YMNM

<400> SEQUENCE: 41

Tyr Met Asn Met
1
```

USE OF MONOCLONAL ANTIBODIES SPECIFIC TO THE O-ACETYLATED FORM OF GD2 GANGLIOSIDE FOR THE TREATMENT OF CERTAIN CANCERS

FIELD OF THE INVENTION

The present invention provides new methods for the diagnosis and the therapy of cancers with cells expressing the O-acetylated form of GD2 ganglioside. These methods include essentially the use of recombinant monoclonal antibodies or fragments thereof which recognize O-acetylated GD2 and which do not recognize the sound cells and the nerve fibers of the peripheral nervous system. These new methods will be more specific to cancer cells and will reduce the toxicity of the treatments compared with antibodies and derivatives previously used for treating these cancers.

PRIOR ART

Tumor cells have on their surface a number of antigenic determinants. Among these antigenic determinants, some are antigens specific to the tumor. These tumor antigens are expressed mainly or even exclusively at the surface of cancer cells.

These human tumor antigens induce the production, by the immune system of different species like mice, of molecules known as antibodies which have the characteristic of recognizing specifically the antigen molecules from which they originate.

This specific recognition between a monoclonal antibody and its human tumor antigen is particularly advantageous for cancer immune targeting. In fact, it makes it possible for detection agents for diagnosing or toxic agents for treating tumors to concentrate on the diseased tissues or organs. These detection or toxic agents can include optionally radioactive, chemical or biological compounds artificially linked to antibodies before or after their administration. These agents can also be biological compounds naturally occurring in the patient (components of the complement, chemokines, cytokines, cytotoxic cells, for example T or NK lymphocytes) recruited to the tumor cells by antibodies.

Gangliosides are constituents of the cell membrane and some of them have been characterized as being tumor antigens. It could be demonstrated that GD2 ganglioside is highly expressed in human cancers of neuroectodermic origin such as in particular melanomas, glioblastomas, small cell lung carcinomas and neuroblastomas. The list of above-mentioned tumor pathologies is not exhaustive. Retinoblastomas and osteosarcomas also express GD2 ganglioside. Some ovary cancers also express GD2 ganglioside. The GD2 ganglioside is a glycolipid acid formed by a ceramide combined with an oligosaccharide having the sequence glucose galactose N-acetyl-galactosamine. To the galactose molecule are linked two molecules of sialic acid. The terminal sialic acid can be modified by adding an O-acetyl moiety to produce O-acetylated GD2. By means of antibodies specific to GD2 which also recognize its O-acetylated form, it could be shown that certain types of cancers, in particular tumors of neuroectodermic origin, express GD2 and its O-acetylated form, O-acetylated GD2, in varying proportion.

Several monoclonal anti-GD2 antibodies produced in the mouse have been described. The therapeutic use of anti-GD2 monoclonal antibodies, 14.G2a and 3F8, belonging to the class of IgG2a and IgG3 mouse immunoglobulins, respectively, has been tested in clinical studies.

These studies have pointed up several adverse side effects inherent to mouse monoclonal antibodies.

One of these adverse effects is an allergic or anaphylactic reaction which can result from an immune response developed by man against mouse antibodies.

In order to solve this immunogenicity problem of monoclonal antibodies produced in the mouse, it is possible by using genetic engineering techniques to make chimeric antibodies. "Chimeric" antibodies refer to a genetically modified antibody in which a more or less important part of the genetic information codes for the mouse antibody by the corresponding portion of a human antibody. Generally, the variable regions of the heavy and light chains ($V_H$ and $V_L$) of murine antibody are conserved, whereas the rest of the antibody molecule is derived from a human antibody. These chimeric antibodies conserve the specific recognition of the tumor antigen inherent to mouse monoclonal antibody while having the physical and effector properties inherent to the human antibody. Thus, clinical studies have shown that the chimeric antibodies ch.14G2a and ch.14.18 display a reduced immunogenicity and an increased serum half-life compared with the mouse monoclonal antibody they derive from. Further, it has been shown that mouse anti-GD2 monoclonal antibodies display an increased ability to recruit human effector cells when they are chimerized, whereas mouse antibodies only have a limited ability to recruit these human effector cells.

Identifying murine antibodies to human antibodies can be taken further by only conserving from the murine antibody amino acids in the so-called CDR regions or "complementarity-determining regions" comprising the antigen attachment site and therefore determine the antibody specificity. "Humanized" antibodies mean a genetically modified antibody in which only the CDR amino acids are conserved, plus optionally a few amino acids close to these CDR regions of the starting mouse antibody, and in which the rest of the molecule is derived from a human antibody.

Disadvantages of the Prior Art

For therapeutic or diagnostic in vivo use of monoclonal antibodies it is necessary that the latter meet the particular specificity, affinity and non-toxicity requirements. However the clinical studies carried out on monoclonal and chimeric anti-GD2 antibodies demonstrate a major adverse side effect, which is not solved by chimerization or humanization and which is anti-GD2 antibody neurotoxicity. In fact, patients with a cancer of neuroectodermic origin administered with anti-GD2 antibodies have suffered from pains during administration of the antibodies and some of these patients have developed a peripheral nervous system neuropathy. These effects are explained by the presence of GD2 gangliosides at the surface of the nerve fiber cells of the peripheral system.

It is thus clear that this nerve toxicity inherent to the use of anti-GD2 antibodies has limited the clinical development of immunotherapy with these antibodies. Yet the great number of GD2 antigenic targets remains a factor of major value for immune targeting of cancers of neuroectodermic origin.

One approach which should help solving the problem of nerve toxicity would be to use an antibody recognizing a tumor antigen related to cancers of neuroectodermic origin differing from GD2 ganglioside and not recognizing the peripheral nerve fibers.

A few years ago, the inventors carried out a series of mouse immunizations in order to produce anti-GD2 antibodies. Several anti-GD2 antibodies could thus be isolated and their characterization resulted in particular in the identification of an antibody of the mouse IgG3 class designated as 8B6 which specifically recognizes a GD2 ganglioside molecule slightly modified by the presence of an O-acetyl moiety. This work, and in particular this 8B6 antibody is described in the article <<Variable Region Gene Segments of Nine Monoclonal Antibodies Specific to Disialoganglisosides (GD2, GD3) and their O-Acetylated Derivatives>>, Cerato et al., Hybridoma Volume 16, Number 4, 1997, 307-316, incorporated herein by reference.

The structure of this antibody was examined, but its development was not carried out further. In fact, there appeared to be then no particular interest in this novel antibody compared with known anti-GD2 antibodies. Contrary to the non-acetylated form of GD2, the issue of tissue distribution in men of O-acetylated GD2 is still not well-documented because of the lack of sensitive detection methods such as methods relying on the use of monoclonal antibodies specific to the acetylated form of GD2. It was therefore expected that the clinical use of this novel antibodies was likely to cause the same neurotoxicity problem as the use of anti-GD2 monoclonal antibodies. Further, no cytotoxic activity of the 8B6 antibody has been demonstrated and IgG3 antibodies are not easily handled due to their tendency to agglomerate.

Objects of the Invention

The monoclonal antibodies specific to O-acetylated GD2 ganglioside not recognizing GD2 ganglioside could have the advantage of not recognizing the peripheral nerve fibers and therefore of not causing nerve toxicity. Such antibodies could therefore have a major advantage in immune targeting of certain types of cancers like human cancers of neuroectodermic origin expressing GD2 ganglioside in its O-acetylated form compared with anti-GD2 monoclonal antibodies.

Such antibodies can be obtained by a variety of techniques known by those skilled in the art. Some of these techniques comprise first immunizing animals, in particular rodents including mice, rats or hamsters, lagomorphs including rabbits, camelidae, including lamas. The immunogenic material, i.e. the preparation containing the antigen against which the antibodies are to be raised, can be either the glycolipid itself, whether purified or contained in a raw or partially purified mixture, or the glycolipid or one of its portions, in particular the glycosylated hydrophilic portion, optionally covalently coupled to proteins or lipids as a "carrier" to stimulate the immune response. In another immunization process, the immunogenic material can be prepared from cells expressing the antigen, obtained by cell culture of lines of tumor cells or of primary cells obtained from tumor samples. Useful lines include in particular animal cell lines, like murine or human EL-4 thymoma, e.g. human IMR-32 neuroblastoma, human U87MG glioblastoma, HCI-H82 small cell lung carcinoma and human M21 melanoma.—These cells can then either be administered as whole, living or fixed cells, or be fractionated to only inject for example a partially purified fraction containing cell membrane or cytoplasm components.

These immunogenic materials can be administered to animals by various routes, in particular subcutaneous, intraperitoneal or intra-muscular, alone or in the presence of an adjuvant, in particular alum or Freund's adjuvant. The immunizations can be repeated at a frequency ranging from a few days to a few months.

Three general methods can provide antibodies which can be used in industrial applications. The first one comprises taking a blood sample from the immunized animals and extracting therefrom, with processes known by those skilled in the art, fractions containing the more or less purified antibody (serum or plasma, total immunoglobulins). The antibodies can be further purified by chromatographic techniques or immunoadsorption. The second method comprises sampling cells capable of synthesizing the antibodies, including spleen or lymph node cells, and immortalizing them, in particular by viral transformation or by somatic hybridization according to processes known by those skilled in the art. Among the immortalized cells, the cloning provides a screening of the cells producing the antibodies of interest, and the cell culture makes it possible to isolate these antibodies from the culture supernatants and to purify them in large quantities. Lastly the third method comprises isolating the RNA from cells capable of synthesizing antibodies, in particular spleen, lymph node or peripheral lymphocyte cells sampled from animals, whether immunized or not, or even from humans, and compiling cDNA libraries from which the sequences of the antibodies of interest will be selected by screening according to methods known by those skilled in the art, and in particular by expression of this library at the surface of a bacteriophage also known as phage display expression system. The construction of combination libraries of human VH and VL regions, expressed at the surface of filament phages ('phage display'), in the form of 'single chain' fragments ('single chain Fv', scFv), linking a VH region and a VL region or of F(ab) fragments, consisting of the light chain related to VH-CH1 peptide segment, the latter corresponding to the first domain of the constant region.

The antibodies of the present invention can be selected from antibodies obtained by any of the methods described above in that they recognize the O-acetylated GD2 antigen and not the non-O-acetylated GD2 antigen, which property will be designated as a required specificity. This selection can be carried out during the antibody isolation process, for example by propagating only the antibody-producing cells having the required specificity. Alternatively, it will be possible to carry out a search among the antibodies already isolated, to select those having this specificity. For this purpose, a variety of methods can be used, in particular indirect immunofluorescence on cells for distinguishing which antibodies will recognize the cells known to express O-acetylated GD2, in particular IMR-32, from the ones which will also recognize cells expressing GD2 but not O-acetylated GD2, in particular Neuro 2A. It will also be possible to use an ELISA immunoenzymatic assay on desiccated cells for selecting antibodies which only bind to the cells expressing O-acetylated GD2 and not to those expressing only GD2. It will be possible also to select antibodies having the required specificity using silica thin layer chromatography to separate the glycolipid components of the cells expressing both O-acetylated GD2 and GD2, in particular IMR-32, by only keeping those antibodies which only label the band corresponding to O-acetylated GD2. It will be possible to confirm this result by breaking down through alkali treatment O-acetylated GD2 in the lipid extract and by checking that the labeling is effectively abolished Implementation examples of these techniques for confirming the specificity of the antibodies of the present invention are given in the detailed description of the invention, below. Other methods, for the same purpose, can be developed by those skilled in the art.

The antibodies of the present invention can be modified by a variety of techniques known by those skilled in the art to be suitable for various applications. It will thus be possible to use the methods known from the prior art to produce simple chain scFv antibodies as well as a variety of fusion proteins keeping the ability to bind the antigen. It is known in particular to entirely modify the so-called constant regions of the antibodies, for example for exchanging murine constant regions against constant regions from human antibodies, without losing antigen recognition. The construction of a chimeric antibody comprises isolating the DNA encoding the VH region and the VL region of a mouse monoclonal antibody and binding it to the DNA encoding the constant regions H and L of a human immunoglobulin. Such a genetic construction provides a human, hybrid antibody, the constant portion of which is not at all or very slightly immunogenic in man (in general, the constant region of human IgG1 and the human Ckappa region). It is further known to conserve only the regions necessary antigen recognition, the so-called hypervariable regions, the complementarity-determining regions or CDR, and to replace all the others to carry out was is known as a "'humanization' of the antibody. The resulting mixture of these proteins will be designated by the term 'artificially modified antibodies' in order to make the description easier.

Some of these proteins are particularly interesting for the antibodies of the present invention. For example, the artificially modified O-acetylated anti-GD2 antibodies conserving the recognition of O-acetylated GD2 ganglioside without recognizing GD2 ganglioside could have a major advantage compared with mouse O-acetylated anti-GD2 monoclonal antibodies in that they would have superior physical and effector characteristics.

The artificially modified antibodies specific to O-acetylated GD2 should have a sufficient affinity for the corresponding antigen so as to prevent as much as possible the diffusion of this antibody, optionally carrying a toxic or therapeutic substance into the sound tissues or cells. Within the scope of the present invention, the affinity for O-acetylated GD2 ganglioside shall be higher than $10^{-7}$ mol/liter. The affinity of these antibodies can be increased by techniques known by those skilled in the art. Thus, the expression of antibody fragments at the surface of bacteriophages constitutes a valuable tool for searching high affinity mutants from a given scFv. It is thus possible to mimic the affinity maturation observed during the development of the immune response. The techniques for random mutations or targeted mutations, followed by a selection by repeated cycles of immuno-adsorption/elution have thus been successfully used and have provided antibody fragments having an affinity of almost 10 times that of the initial fragment.

A particular object of the present invention, which should not be limited by this example, relates to artificially modified antibodies prepared from the 8B6 antibody which is known to display the required specificity, as well as to recombinant proteins using the sequences of the complementarity-determining regions designated SEQ ID NO:2, 3, 4, 6, 7 and 8.

An object of the invention is also to provide modifications of antibodies having the required specificity in order to provide them with useful properties for the diagnosis or therapy of certain cancers. Some of these applications require injecting the antibodies or their derivatives to patients suffering from some cancer conditions. In this case, the derivatives having a sequence more closely related to a sequence of human antibodies will be preferred since they are likely to limit the production by the treated patient of antibodies against the molecule injected, with an increase in tolerance and a possibility of repeated administration. Such derivatives are further likely to favor the antibody response against particular determinants specific to the injected antibody, the so-called anti-idiotypic antibodies, which have been said to have therapeutic value.

For therapeutic applications, the preferred modifications will be those providing cytotoxic activity against tumor cells expressing the target antigen, in the present case O-acetylated GD2.

It is known that only some classes of immunoglobulins have the property of activating the complement or of inducing cell-mediated cytotoxicity. As an example, the 8B6 antibody recognizes O-acetylated GD2 but cannot induce this cytotoxicity effectively enough. Another objet of this invention is therefore to provide antibodies recognizing O-acetylated GD2 and having cytotoxic activity. This can be done in particular by replacing the antibody constant regions by constant regions of antibodies which can elicit this cytotoxicity including constant regions of class 1 human immunoglobulins. The cytotoxic ability will then be increased further, in particular by producing specifically glycosylated, including low-fucosylated, antibodies, for example by having them produced by specially selected or transformed cells. Specific mutations, described in the literature can also be introduced into the antibody sequence for the same purpose.

Another way of making therapeutic antibodies according to the present invention is to combine a cytotoxic agent to an antibody derivative having the required specificity. Said cytotoxic agent can be a toxic chemical, antisense RNAs, including a cytotoxic antitumor drug, which includes taxans, periwinkle alkaloids and derivatives thereof, anthracyclins, alkylating agents, a toxic biological agent, including plant or bacterial toxins, which include ricin or the pseudomonas toxin, or even a radioactive isotope emitting beta particles, such as 131-iodine, 90-yttrium, 177-lutetium, 186-rhenium or 67-copper, or Auger electrons, such as the 111-indium, or even alpha particles, such as 213-bismuth, 212-bismuth or 211-astatine, with these examples being in no way limitative to the scope of the invention. The antibody can also be produced by molecular engineering methods, known by those skilled in the art, in the form of a fusion protein combined with a cytokine. The cytokines used are essentially members of the families of interleukins such as interleukin-2 (IL-2), IL-4, IL-5, IL-6, IL-7, IL-10, IL-12, IL-13, IL-14, IL-15, IL-16 and IL-18, hematopoietic growth factors such as GM-CSF (granulocyte macrophage Colony Stimulating Factor) or G-CSF (granulocyte Colony Stimulating Factor), the Tumor Necrosis Factor (TNF), and chemokines. The resulting antibody-cytokine fusion protein has the biological properties of the cytokine and the specificity of the antibody from which it is derived.

The antibodies of the present invention can also be applied advantageously to diagnosis, whether the latter is done in vitro for detecting the presence of O-acetylated GD2 antigen in cell or biological fluid samples, following any of the techniques known by those skilled in the art, or carried out in vivo by administration of an antibody derivative modified so as to become detectable by one of the medical imaging techniques known, i.e. scintigraphy or position emission tomography. In this case, the antibody derivative will be combined with a radioactive isotope emitting gamma photons, such as 131-iodine, 123-iodine, 111-indium, or 99m-technetium for scintigraphic imaging or single photon tomography, or to a position-emitting isotope, such as 18-fluorine, 124-iodine, 86-yttrium, 64-copper, 44-scandium, for position emission tomography, again without these examples being limitative to the scope of the invention.

The antibodies of the present invention can be combined to toxic or radioactive compounds. The toxic products are chemically, or covalently coupled to antibodies by a variety of chemical bonds, including ester, amide, disulfide or thioether bonds. The radioactive atoms are coupled either directly by electrophilic substitution (in the case of iodine isotopes) or nucleophilic substitution (in the case of 18-fluorine), or through a radiolabeled reactive synthon, including the Bolton and Hunter reagent for iodine isotopes, or stannylated activated esters for iodine isotopes or 211-astatine, or even by means of a chelating agent when it is a radioactive metal. In the latter case, it is within the knowledge of those skilled in the art to choose among the chelating agents which one will provide together with the metal a complex having good stability in the biological fluids. Thus DTPA can be advantageously used with 111-indium, but DOTA will be preferred for labeling with 90-yttrium.

The antibodies of the present invention can be used in methods known by those skilled in the art in which the toxic or detectable agent is not bound directly to the antibody, but is bound on the contrary to a molecule of low molecular weight administered in a second stage, after administration to the patient of an antibody derivative capable of recognizing this small molecule in vivo. In this case the antibody derivative is in particular a bispecific antibody or an immunoconjuguate, or a fusion protein between an antibody derivative and an avidine. This approach can be advantageously used with the antibodies of the present invention for in vivo diagnosis and treatment of tumors.

The antibody of the present invention and the 'derivatives', 'antibody derivatives' or 'derivative materials' can therefore be advantageously used for diagnosis or therapy of such tumors. These include tumors of neuroectodermic origin including melanomas, small cell lung cancers, gliomas and neuroblastomas. The products of the present invention can be applied advantageously to the detection and treatment of these tumors, in particular when they are disseminated or do not respond to existing treatments.

SUMMARY OF THE INVENTION

The present invention discloses the use of antibodies for immune targeting of human cancers of neuroectodermic origin such as melanomas, glioblastomas, small cell lung carcinomas and neuroblastomas.

In all the various aspects of the invention described above, it has been found very surprisingly that a monoclonal antibody specific to O-acetylated GD2 does not attach to the nerve fibers expressing GD2 while recognizing tumor cells expressing GD2 ganglioside and its O-acetylated form. Such antibodies have therefore a specificity which is restricted to tumor cells of neuroectodermic origin, and do not recognize the peripheral nerve fibers. The increased specificity results in a reduced toxicity in therapeutic applications resulting in particular from the absence of attachment on normal peripheral nerve tissues which is observed with antibodies recognizing GD2 ganglioside. The present invention therefore includes the use of such antibodies for diagnosis and therapy of cancers with an increased specificity and a reduced toxicity compared with antibodies recognizing GD2.

The antibodies of the present invention have a cytotoxic activity for tumor cells which they recognize, either intrinsically (this is one of the reasons why it is chimerized or humanized), or because they act as vectors for toxic agents, in particular radioactive agents.

The present invention therefore includes any monoclonal chimeric or humanized antibody only recognizing the O-acetylated form of GD2 ganglioside, or a fragment of this antibody, said antibody or said fragment recognizing O-acetylated GD2 molecules expressed by tumor cells and not recognizing GD2 molecules expressed at the surface of the peripheral nerves.

The present invention also provides antibodies in which some amino acids were replaced by others using molecular genetic techniques known by those skilled in the art, in particular for modifying the properties of the original antibody, in particular for decreasing its immunogenicity, or for increasing its toxic activity or even for speeding up or slowing down its clearance after injection.

Advantageously the artificially modified monoclonal antibody or a fragment thereof according to the invention is characterized in that it is a kappa-IgG having an affinity of more than $10^{-7}$ mol/liter for O-acetylated GD2 and having an affinity of at least ten times lower for GD2 itself, with said antibody or said fragment being mono or bi-specific.

In particular, but not exclusively, the invention provides any artificially modified monoclonal antibody or a fragment thereof wherein the complementarity-determining regions of the H chain variable region have amino acid sequences represented in SEQ ID NO:2, SEQ ID NO:3 and SEQ ID NO:4, and the complementarity-determining regions of the L chain variable region have amino acid sequences represented in SEQ ID NO:6, SEQ ID NO:7 and SEQ ID NO:8.

In particular, but not exclusively, the invention provides any artificially modified monoclonal antibody or a fragment thereof, having a heavy chain obtained by linking the cDNA coding for the variable region of the heavy chain of an non-human antibody to the cDNA coding for the constant region of a human immunoglobulin and having a light chain obtained by linking the cDNA coding for the variable region of the light chain of the same non-human antibodies to the cDNA coding for the constant region of the light chain of a human immunoglobulin characterized in that said non-human antibody is the mouse 8B6 monoclonal antibody and said artificially modified antibody is raised against O-acetylated GD2 ganglioside and does not recognize the peripheral nerve fibers.

In particular, but not exclusively, the invention provides any artificially modified monoclonal antibody or a fragment thereof having a heavy chain variable region with an amino acid-deduced sequence represented by SEQ ID NO:1 and having a light chain variable region with an amino acid-deduced sequence represented by SEQ ID NO:5.

Preferably, the artificially modified monoclonal antibody or a fragment thereof according to the invention, is the KM8B6 antibody which can be obtained by means of the CHO cell line or a fragment thereof.

The invention also provides any pharmaceutical molecule derived from the artificially modified antibody or a fragment thereof according to the invention wherein the antibody or a fragment thereof is coupled with a molecule X, where X is a toxic molecule, a drug, a pro-drug, or a second antibody irrespective of its specificity.

According to one embodiment, said toxic molecule is a toxic chemical, biological or radioactive molecule, said molecule being designed to kill tumor cells expressing O-acetylated GD2 ganglioside.

The invention also provides a method for the treatment of cancers expressing the O-acetylated form of GD2 ganglioside selected in the group comprising neuroblastomas, lymphomas, melanomas, glioblastomas and small cell lung cancers, said method comprising administering to a patient in need thereof an antibody or a fragment thereof that specifically binds to O-acetylated GD2 ganglioside and which is coupled to a biological toxic molecule (BTM), wherein said antibody or a fragment thereof has the complementarity-determining regions of the H chain variable region comprising amino acid sequences represented in SEQ ID NO:2, SEQ ID NO:3 and SEQ ID NO:4 and has the complementarity-determining regions of the L chain variable region comprising amino acid sequences represented in SEQ ID NO:6, SEQ ID NO:7 and SEQ ID NO:8, wherein said antibody has an affinity of at least ten times lower for the non O-acetylated form of GD2 ganglioside and wherein an effective amount of said antibody or a fragment thereof coupled to a biological toxic molecule (BTM) provides cytotoxic activity against said cancer cells.

In particular, the antibody fragment coupled to the BTM is in the form of single chain fragments of heavy and light chains variable regions (scFv). By "scFv" is intended antibody fragment comprising the $V_H$ and $V_L$ domains of antibody, wherein these domains are present in a single polypeptide chain. In some embodiments, the scFv polypeptide further comprise a polypeptide linker between the $V_H$ and $V_L$ domains, which enables the scFv to form the desired structure for antigen binding. By "scFv" is also intended construct which provides the binding domain of an antibody in single chain form as, for example, which may include only one or more of the CDRs of an antibody. For review of scFv, see Plucktun in the Pharmacology of Monoclonal Antibodies, vol. 113, Rosenberg and Moore eds., Springer-Verlage, new-York, pp. 269-315 (1994).

By "biological toxic molecule (BTM)" is intended a polypeptide encoded by a nucleic acid sequence or chemically synthetized. The polypeptide can have a biological function within the cell, independently of the antigen binding activity of the antibody or a fragment thereof. For example, the biological activity of the polypeptide may relate to cell-signaling.

Preferably, the coupled antibody or a fragment thereof and BTM are covalently linked to form a chimeric antigen receptor (CAR). By "CAR" is intended an artificial hybrid protein or polypeptide containing the antigen binding domains of an antibody or a fragment thereof, linked to T-cell signaling domains. CARs are molecules able to redirect T-cell specificity and reactivity toward a selected target in a non-MHC-restricted manner, thus exploiting the antigen-hinging properties of monoclonal antibodies. When expressed in T-cells, CARs offer the ability to said T-cells to recognize antigen independently of antigen processing, thus bypassing a major mechanism of tumor escape. The binding of CARs to a specific antigen elicits an immune response.

The T-cells engineered to express CARs include all types of immune cells expressing CD3 including T-helper cells (CD4+ cells), cytotoxic T-cells (CD8+), T-regulatory cells (Treg) and gamma-delta (γδ) T cells. A cytotoxic cell is a cell capable of mediating cytotoxicity responses such as those of CD8+ T cells, natural-killer (NK) cells and neutrophils.

The CARs used in the method according to the invention comprise an ectodomain, a transmembrane domain and an endodomain.

Preferably, the ectodomain of the CARs used in the method of the invention comprises a specific tumor associated antigen binding domain. More preferably, the ectodomain of the CARs used in the method of the invention comprises an O-acetylated GD2 ganglioside antigen binding domain having the CDRs as defined by the sequences of SEQ ID NO:2, 3, 4, 6, 7 and 8 and an extracellular hinge domain. The specificity of the CARs used in the method of the invention derived from the scFv region assembled from the antigen binding regions of the 8B6 mAb. The CDRs of SEQ ID NO:2, 3 and 4 are specific of 8B6 $V_H$ as disclosed by SEQ ID NO:29. The CDRs of SEQ ID NO:6, 7 and 8 are specific of 8B6 $V_L$ as disclosed by SEQ ID NO:31. SEQ ID NO:31 derives from SEQ ID NO:5, wherein the signal peptide has been removed and the last two amino acid residues in Cter are missing due to the cloning procedure.

As previously mentioned, a linker, notably a flexible linker, can be disposed between the VH and the VL domains to form the desired structure for antigen binding. A linker can be a peptide of between 6 to 40 amino acid residues. The use of small amino acids such as alanine and glycine are of use in creating flexible linker. Exemplary flexible linkers include glycine polymers (G)n, glycine-serine polymers such as for example $(GS)_n$, $GSGGS_n$, $GGGS_n$ and $GGGGS_n$, where n is an integer of at least one, glycine-alanine polymers or glycine-serine polymers, or other flexible linkers known in the art. Preferably, the flexible linker is a $GGGGS_n$, where n is between 1 to 4. More preferably, the flexible linker is a $GGGGS_3$ as disclosed by SEQ ID NO:30.

In particular, the extracellular hinge domain is derived from IgG1, IgG2, IgG3 or IgG4 hinge domain. CH1, CH2 and CH3 domains from different IgG istotypes can be used to obtain an extracellular domain. Preferably, the CH2 and CH3 domain of a human IgG1 have been incorporated within the sequence of the CARs used in the method of the invention. As an example, a human engineered IgG1 Fc region is illustrated by SEQ ID NO:32.

The ectodomain of the CARs used in the method of the invention can further comprises a signal peptide which allows the correct routing of the CARs polypeptide to the cytoplasmic membrane of the T-cells expressing CARs. For example, a functional signal peptide in T-cell can be a fragment of an Ig kappa such as this disclosed by SEQ ID NO:28. The fusion of SEQ ID NO:28 and 29 corresponds to the sequence of SEQ ID NO:1 wherein the alanine residue in Cter has been removed during the cloning procedure.

Preferably, the transmembrane domain of the CARs used in the method of the invention comprises a T cell receptor transmembrane domain. T cell receptor transmembrane domain is issued from a transmembrane protein able to form a complex with the T cell receptor for antigen (TCR).

In particular, the T cell receptor transmembrane domain comprises part or all of one or more of TCR Zeta chain (CD3ζ), CD28, OX40/CD134, 4-1BB/CD137/TNFRSF9, FcεRIγ, ICOS/CD278, ILRB/CD122, IL-2RG/CD132, and CD40.

Preferably, the endodomain of the CARs used in the method of the invention comprises a T cell receptor signaling domain. This signaling domain contains signaling motifs such,—i.e. ITAMs motifs-, which allow intracellular signaling. The effector function of T cell relies on the collaboration of the T cell receptor for antigen (TCR) with intracellular signaling domains that activate the T cell. Once the ligand binds to the TCR, intracellular signaling domains are assumed to be responsible for intracellular signaling. The signaling domain are derived from cytoplasmic region of CD3 zeta or the Fc receptor gamma chains.

In particular, the T cell receptor signaling domain comprises part or all of one or more of TCR Zeta chain (CD3ζ), CD28, OX40/CD134, 4-1BB/CD137/TNFRSF9, FcεRIγ, ICOS/CD278, ILRB/CD122, IL-2RG/CD132, and CD40.

In some cases, the T cell receptor signaling domain is derived from a portion of the transmembrane protein CD28 (also known as Tp44). For example, a suitable T cell receptor signaling domain can comprise an amino acid sequence having at least about 93%, at least about 95%, at least about 98% or 100% amino acid sequence identity to the amino acid sequence of SEQ ID NO:33. Moreover, the amino acid sequences derived from SEQ ID NO:33 holds the same biological function in terms of phosphorylation activity as CD28. Notably, the presence of a phosphoinositide 3-kinase (PI3K) binding motif such as YMNM motif (SEQ ID NO: 41) within the proximal intracytoplasmic domain of the protein or protein derived CD28 is needed. PI3K has been reported to bind to the YMNM phosphotyrosine, which leads to PI3K activation. Other distal proline-rich motifs such as PRRP and PYAP are also involved in the signal transduction cascade by their binding respectively to Itk, and the three proteins Grb2, filamin-A and Lck.

In some cases, the T cell receptor signaling domain is derived from a portion of the transmembrane protein CD3ζ. For example, a suitable T cell receptor signaling domain can comprise an amino acid sequence having at least about 95%, at least about 98% or 100% amino acid sequence identity to the amino acid sequence of SEQ ID NO:34. Moreover, the amino acid sequences derived from SEQ ID NO:34 holds the same biological function in terms of signal transducing as CD3ζ. At least one ITAM motif in the cytoplasmic portion of CD3ζ has to be present for allowing CARs to transmit signal within the transformed T-cell. Once the binding of O-acetylated antigen to the O-acetyl-GD2 CAR constructs of the invention occurs, the two tyrosine residues of the cytoplasmic ITAM motifs in the CD3ζ chain or in the derived CD3ζ chains become phosphorylated by the Src-family kinase Lck.

Preferably said tumor cells targeted by the pharmaceutical molecules according to the invention are neuroblastoma, melanoma, glioblastoma or small cell lung cancer cells.

Preferably the pharmaceutical molecules according to the invention are mutated at their Fc region by the adjunction of sugars, thus modulating activation of the immune cells and complement system molecules.

The invention also provides any molecule for the diagnosis of cancers displaying expression of O-acetylated GD2 ganglioside at the surface of tumor cells, said molecule being derived from the artificially modified antibody or a fragment thereof according to the invention, wherein said antibody or said fragment is bound to an agent for detecting the antibody or said fragment by fluorescence or radioactivity.

The invention therefore relates to any use of an artificially modified antibody or a fragment thereof according to the invention and/or of a molecule according to the invention, for the manufacture of a drug for therapeutically treating a cancer having cells expressing the O-acetylated form of GD2 ganglioside or for the manufacture of a product for diagnosing such cancer.

The present invention further provides any use of the 8B6 monoclonal antibody (described in the article 'Variable Region Gene Segments of Nine Monoclonal Antibodies Specific to Disialogangliosides (GD2, GD3) and their O-Actylated Derivatives', Cerato et al., Hybridoma Volume 16, n° 4, 1997, 307-316) for the manufacture of a pharmaceutical molecule wherein said antibody is bound to a toxic chemical, biological or radioactive agent, said molecule being designed to kill tumor cells expressing O-acetylated GD2 ganglioside.

In particular, but not exclusively, the invention provides such a use where said cells are neuroblastoma, melanoma, glioblastoma or small cell lung cancer cells.

In particular, but not exclusively, the invention provides such a use where said therapeutic molecule is mutated at its Fc region by the adjunction of sugars, thus modulating activation of the immune cells and complement system molecules.

The invention also provides any use of the 8B6 monoclonal antibody for the manufacture of a molecule for the diagnosis of cancers expressing O-acetylated GD2 ganglioside at the surface of tumor cells, said molecule being derived from said antibodies, wherein said antibody is bound to an agent for detecting the antibody by fluorescence or radioactivity.

The invention also provides any sequence of DNA coding for the artificially modified antibody according to the invention as well as any expression vector comprising such a DNA sequence functionally linked to a promoter.

The invention also provides any cell, in particular an animal cell, comprising such an expression vector, as well as any non-human transformant producing the artificially modified antibody according to the invention.

Lastly, the invention provides any process for the production of artificially modified antibodies for O-acetylated GD2 ganglioside, said process comprising the expression of the DNA sequence in a cell or a non-human transformant under suitable conditions, and antibody recovery.

Preferably, the cell or the transformant is cultured under conditions in which the antibody builds up.

BRIEF DESCRIPTION OF THE FIGURES

FIG. 3 illustrates the construction of the plasmid, pcDNA3® KM8B6L.

FIG. 4 illustrates the nucleotide sequence and the amino acid-deduced sequence of the light chain of the artificially modified antibody KM8B6 (SEQ ID NO: 36).

FIG. 5 illustrates the construction of the plasmid, pBluescript® II SK (+) 60C3 L-VH.

FIG. 9 illustrates the nucleotide sequence and the deduced amino acid sequence of the artificially modified antibody heavy chain KM8B 6(SEQ ID NO: 37).

FIG. 15 shows the results of the toxicity study (ADCC) Percent ADCC activity of the artificially modified KM8B6 antibody and of the mouse 8B6 mAb from which it is derived. *Rituxan® anti-CD20 antibody used as negative control.

FIG. 17 illustrates the construction of the O-Acetyl-GD2 (8B6)-based CARs. The schematic representation of the O-Acetyl-GD2 (8B6)-based CARs is illustrated in panel A. CARs contain the signal peptide (SP), VH: murine IgG3 8B6 heavy chain; L: Linker (GGGSx3); VL: murine IgG3 8B6 light chain linked to the hinge and Fc region of the engineered IgG1. These were linked to the human CD28 transmembrane (TM) and intracellular (IC) domains (residues 151-220) and the CD3 zeta intracellular domain (residues 52-164) for CAR 8B6-28Z or only the CD28 three first cytoplasmic amino acids after the transmembrane domain (residues 179-181) for CAR 8B6-28. Amino acids sequence of O-Acetyl-GD2 (8B6)-CD28Z CAR (SEQ ID NO:35) is illustrated in panel B. The sequence is composed of following parts indicated below the sequence.

Figure 18:
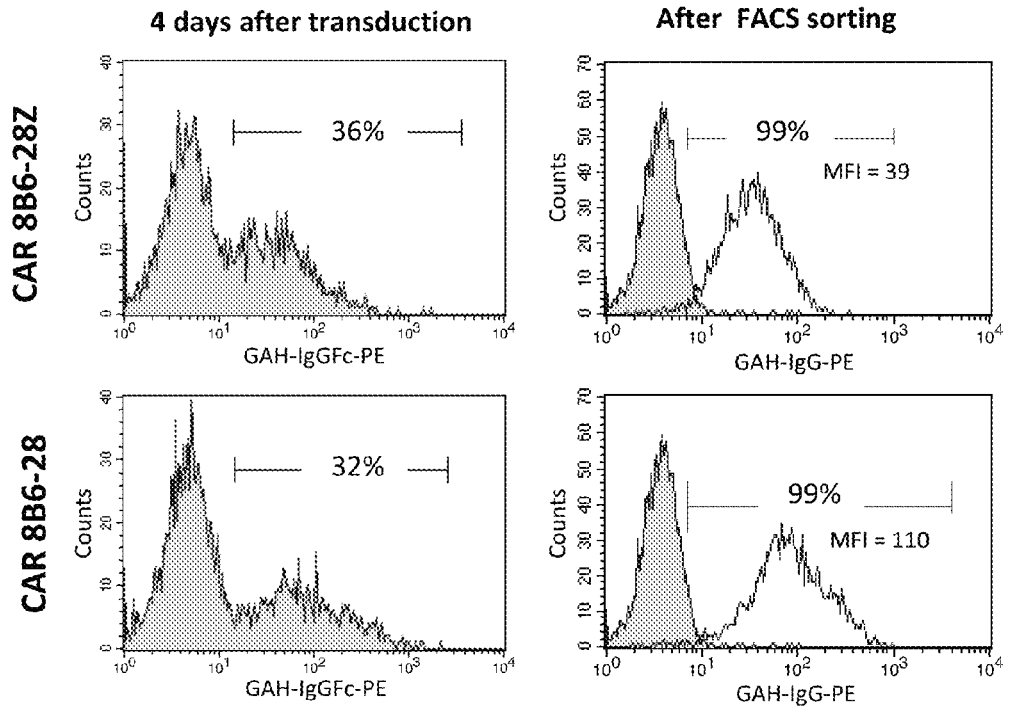

FIG. 18 shows the results of the surface expression of CAR 8B6-28Z and CAR 8B6-28 on human NK-92 cell line. Four days after retroviral transduction, surface expression of CARs was determined by flow cytometry with Goat F(ab')2 polyclonal antibody to human IgG-Fc (PE)(GAH-IgG-PE) (left panel). Twelve days after transduction, CARs expressing NK-92 cells were FACS sorting using FACS ARIA cytometer (right panel). In right panel, mock-transduced NK-92 cells were used as control (grey areas). Mean fluorescence intensities (MFI) are indicated.

Figure 19:
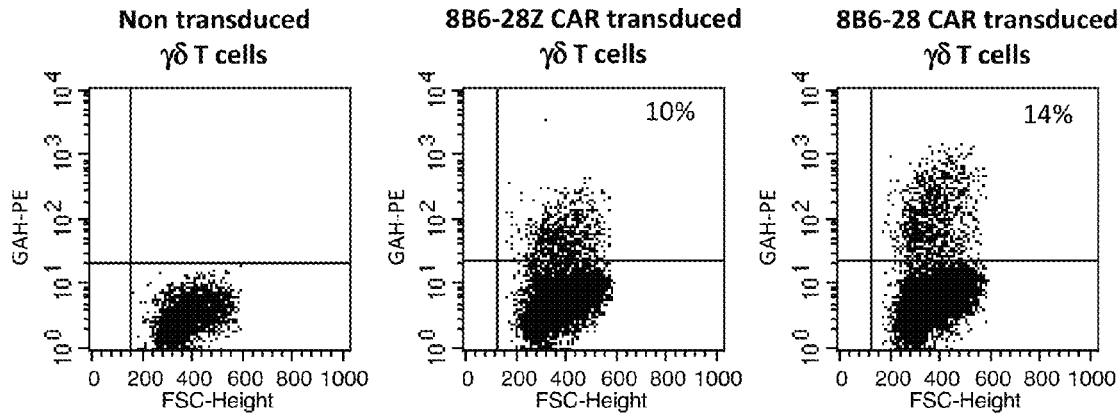

FIG. 19 shows the results of the surface expression of CAR 8B6-28Z and CAR 8B6-28 on human γδ T cells. After retroviral transduction, transduction levels were assessed by staining the CAR-transduced γδ T cells with a PE-conjugated Goat F(ab')2 polyclonal secondary antibody to human IgG-Fc, pre-absorbed) (abcam, Cambridge, UK). In left panel, mock-transduced γδ T cells were used as control. Percentages of CAR-positive cells are indicated in dot plots.

DETAILED DESCRIPTION OF THE INVENTION

Production of Artificially Modified KM8B6 Antibodies

1. Preparation of cDNA Coding for the Variable L-VL Region of the Mouse Monoclonal Antibody 60C3

(a). Extraction of Total RNA from the 60C3 Hybridoma, Producing the Monoclonal 60C3 Antibody.

The total RNA is extracted from 106 60C3 hybridoma cells in exponential growth phase by means of a RNAble reagent (EUROBIO, Courtaboeuf, France) according to the supplier's directions. The total RNA concentration is determined by measuring the optical density at 260 nm.

(b). Obtaining the Nucleotide Sequence of 60C3 L-VL cDNA

Gene amplification of the cDNA coding for the 60C3 L-VL variable region was obtained from the messenger RNAs by RACE-PCR to provide the nucleotide sequence coding for the signal peptide (L) combined with its variable region (VL). This amplification was carried out using the SMART™ RACE cDNA Amplification kit obtained from the company BD Biosciences (San Jose, Calif., USA) according to the supplier's directions. The amount of total RNA used for the back-transcription is 1 μg. The reaction product was diluted in 100 μL of tricine EDTA buffer solution available from the supplier. A 2.5 μL volume of the diluted product was used for gene amplification. The antisense probe specific to 60C3 VL cDNA used is as follows: 5'-60C3 VL 5'-TTT CAG CTC CAG CTT GGT CCC AGC-3' (SEQ ID NO:9). The amplification was carried out by incubating the reaction mixture in a PERKIN-ELMER (PE) DNA thermal Cycler 480 (PERKIN ELMER WELLESLEY, Mass., USA) under the following conditions: 5 cycles (94° C. for 5 seconds, 72° C. for 3 minutes), followed by 5 cycles (94° C. for 5 seconds then 70° C. for 10 seconds followed by 3 minutes at 72° C.) and 25 cycles (94° C. for 5 seconds followed by 69° C. for 10 seconds and 3 minutes at 72° C.). The reaction product of RACE-PCR is analyzed by 1% agarose gel electrophoresis (Q. BIOGENE, Morgan Irvine, Calif., USA) in a migration buffer solution of Tris EDTA pH 8 (40 mM Tris-base (SIGMA CHEMICALS Co), 25 mM EDTA (INTERCHIM, Montlucon, France), 20 mM acetic acid (CARLO ERBA REAGENTI SPA, Rodano, MI, Italy). The products having the expected molecular weight are then purified by means of a QIAquick® Gel Extraction kit (QIAGEN) according to the supplier's directions. The determination of the nucleic acid sequence of the resulting purified products was carried out by the company GENOME EXPRESS (Meylan, France) in order to check for the cDNA sequence coding for the 60C3 L-VL region. The sequence corresponding to the signal peptide combined with the light chain variable region of the 60C3 antibody was thus determined, and probes were designed for cloning the 60C3 L-VL cDNA in the expression vector.

(c). Amplification of 60C3 L-VL cDNA

The amplification of the 60C3 L-VL cDNA was achieved by RT-PCR from a total RNA extract from 60C3 hybridoma cells. The reaction mixture is the following: Oligo d(T)18 0.5 μg (NEW ENGLAND BIOLABS Inc. Beverly, Mass., USA), RNA 1 μg, dNTP 0.5 mM (PROMEGA, Madison, Wis., USA), sterile water qsp 12 μL. This mixture is incubated 5 minutes at 65° C. (dry regulated bath) followed by 2 minutes at 4° C. (melting ice) to denaturate the RNA. To the reaction mixture, 4 μL of 5× First-strand Buffer solution (INVITROGEN LIFE BIOTECHNOLOGIES), 10 mM DTT (INVITROGEN LIFE BIOTECHNOLOGIES), 160 U of Rnasine (PROMEGA) and 800 U of reverse transcriptase (INVITROGEN LIFE BIOTECHNOLOGIES) are then added. The resulting mixture is incubated for 1 hour at 37° C. then at 70° C. for 15 minutes in order to stop the reaction. Copies of 60C3 L-VL cDNA are obtained by PCR gene amplification using the following synthetic oligonucleotides: 5'-BamHI 60C3 L-VL: 5'-AG GGA TCC AAA GAC AAA ATG GAT-3' (sense probe, SEQ ID NO:10) and 3'-XhoI 60C3 L-VL: 5'-TT CAG CTC GAG CTT GGT CCC AGC ACC-3' (antisense probe, SEQ ID NO:11).

The synthetic probes used introduce silent mutations into the DNA sequence that do not result in a change to the amino acid sequence while creating BamHI and XhoI restriction sites required for cloning in the vector.

The reaction medium has the following composition: dNTP (PROMEGa) 500 μM, Taq polymerase (INVITROGEN LIFE TECHNOLOGIES) 1 μL, PCR buffer solution (INVITROGEN LIFE TECHNOLOGIES) 1 μL, cDNA (matrix) 1 μL, MgCl$_2$ (INVITROGEN LIFE TECHNOLOGIES) 1.5 mM, probe 3'-XhoI 60C3 L-VL and probe 5'-BamHI 60C3 500 μM.

The amplification was carried out in an MJ-research PTC 200 thermal cycler (PELTIER THERMAL CYCLER) under the following conditions: 5 minutes at 94° C., then for the next 35 cycles 30 seconds at 94° C., 45 seconds at 55° C. and 1 minute at 72° C.

After checking the PCR products by 1% agarose gel electrophoresis analysis, the 60C3 L-VL cDNA is purified using the QIAquick® Gel Extraction kit (QIAGEN) according to the supplier's directions.

2. Construction of a Recombinant Plasmid Having 60C3 L-VL cDNA: pcDNA3® 60C3 L-VL (a). Digestion of the Vector pcDNA3® and 60C3 L-VL cDNA and Dephosphorylation of the Digested Vector The digestion by restriction enzymes provides a linear vector having cohesive ends required for inserting the cDNA of interest. The digestion is carried out under the following conditions: buffer NEB2 10× (5 μL), BSA 100× (0.5 uL), vector pcDNA3® or 60C3 L-VL cDNA (1 (μg), restriction enzyme BamHI (10U), restriction enzyme XhoI (10U). The restriction enzymes, the reaction buffer solutions and the BSA solution were supplied by New England Biolabs Inc. The reaction is continued for 3 hours in a water-bath at 37° C. The digested vector and insert are purified using a QIAquick® Gel Extraction kit (QIAGEN) according to the supplier's directions. The vector is then dephosphorylated with CIP (NEW ENGLAND BIOLABS INC.) for 1 hour at 37° C. The composition of the reaction mixture is the following: buffer NEB3 10× (5 μL), vector (1 μg), CIP (1 μL). This reaction increases the yield of the ligation by decreasing the percentage of self-ligation of the vector. In fact, suppressing the phosphate moieties at 5' and 3' ends of the released edges by the digestion prevents spontaneous closure of the vector.

(b). Ligation Reaction

The ligation provides insertion of the digested 60C3 L-VL cDNA in the digested and dephosphorylated vector pcDNA3® by using T4 ligase (NEW ENGLAND BIOLABS Inc.). The reaction is carried out further in a water-bath at 16° C. for 16 hours in the following reaction medium: ligation buffer solution 5× (4 μL) (NEW ENGLAND BIOLABS Inc.), digested dephosphorylated vector 200 ng, T4 ligase (400U) (NEW ENGLAND BIOLABS Inc.), purified cDNA 170 ng (for a 1 kb insert). The insert:vector molar ratio is 3:1.

(c). Transformation of Competent Bacteria *E. coli* XL1 Blue (STRATAGENE)

20 μl, of ligation reaction product is added to 100 μL of competent bacteria suspension. The resulting mixture is incubated at 4° C. for 30 minutes. The bacteria are then exposed to a 2 minute thermal shock at 42° C., followed by 2 minutes at 4° C. A 1 mL volume of LB medium is then added and the bacteria are incubated for 1 hour at 37° C. under stirring (250 rpm). The bacteria are recovered by centrifugation for 5 minutes at 4000×g at 4° C. The bacterial pellet is taken up in 10 μL of LB medium before plating on a Petri plate containing the 2XTY agar medium containing 100 μg/mL ampicillin (SIGMA CHEMICALS CO) and 12.5 μg/mL tetracycline (SIGMA CHEMICALS CO). The resistant colonies develop after overnight incubation at 37° C.

(d). Checking for the Presence of the Insert 60C3 L-VL in the Vector pcDNA3® by PCR Isolated colonies are placed under sterile conditions in an extractor hood respectively into a tube containing the PCR reaction mixture: dNTP (PROMEGA) 500 μM, Taq polymerase (INVITROGEN LIFE TECHNOLOGIES) 1 μL, PCR buffer solution (INVITROGEN LIFE TECHNOLOGIES) 10 μL, cDNA (matrix) 1 μL, MgCl$_2$ (INVITROGEN LIFE TECHNOLOGIES) 1.5 mM, probe 3'-XhoI 60C3 L-VL and probe 5'-BamHI 60C3 500 μM.

The amplification was carried out in an MJ-research PTC 200 thermal cycler under the following conditions: 5 minutes at 94° C., then for the next 35 cycles 30 seconds at 94° C., 45 seconds at 55° C. and 1 minute at 72° C. The size of the amplified PCR product is checked with 1% agarose gel electrophoresis analysis. Only those clones which were properly transformed give a PCR product having the expected size.

(e). Production of the Plasmid of Interest pcDNA3® 60C3 L-VL

A sterile tooth-pick is used, and after sampling the colony, is added to 5 mL of LB selective liquid medium containing 100 μg/mL ampicillin (SIGMA CHEMICALS CO) and 12.5 μg/mL tetracycline (SIGMA CHEMICALS CO), and incubated for 16 hours at 37° C. The bacterial dilution is then used for carrying out a plasmid DNA minipreparation using the QIAprep spin miniprep kit (QIAGEN) according to the supplier's directions.

3. Preparation of cDNA Coding for the Constant Region Hu-C Kappa of a Human P3Non2 Monoclonal Antibody (a). Extraction of Total RNA from the P3Non2 Hybridoma, Producing the P3Non2 Monoclonal Antibody.

The total RNA is extracted from 106 P3Non2 hybridoma cells in exponential growth phase with the use of RNAble reagent (EUROBIO, Courtaboeuf, France) according to the supplier's directions. The total RNA concentration is determined by measuring the optical density at 260 nm.

(b). Amplification of hu-C kappa cDNA

The hu-C kappa cDNA amplification was achieved by RT-PCR from a total RNA extract from P3Non2 hybridoma cell. The reaction mixture is the following: Oligo d(T)18 0.5 μg (NEW ENGLAND BIOLABS Inc. Beverly, Mass., USA), RNA 1 μg, dNTP 0.5 mM (PROMEGA, Madison, Wis., USA), sterile water qsp 12 μL. This mixture is incubated for 5 minutes at 65° C. (dry regulated bath) then for 2 minutes at 4° C. (melting ice) to denaturate the RNA. To the reaction mixture are then added, 4 μL of 5× First-strand Buffer solution (INVITROGEN LIFE BIOTECHNOLOGIES), 10 mM DTT (INVITROGEN LIFE BIOTECHNOLOGIES), 160 U of Rnasine (PROMEGA) and 800 U of reverse transcriptase (Invitrogen Life Biotechnologies). The resulting mixture is incubated for 1 hour at 37° C. then at 70° C. for 15 minutes in order to stop the reaction. Copies of 60C3 L-VL cDNA are obtained by PCR gene amplification using the following synthetic oligonucleotides: 5'-XhoI hu-C kappa: 5'-AG CTC GAG CTG AAA CGA ACT GTG GCT GCA C-3' (sense probe, SEQ ID NO:12) and 3'-XbaI hu-C kappa: 5'-CTT CTA GAT TTA ACA CTC TCC CCT GTT GA-3' (antisense probe, SEQ ID NO:13).

The synthetic probes used introduce silent mutations into the DNA sequence that do not result in a change to the amino acid sequence while creating XbaI and XhoI restriction sites required for cloning in the vector.

The reaction medium has the following composition: dNTP (PROMEGA) 500 μM, Taq polymerase (INVITROGEN LIFE TECHNOLOGIES) 1 μL, PCR buffer solution (INVITROGEN LIFE TECHNOLOGIES) 1 cDNA (matrix) 1 μL, MgCl$_2$ (INVITROGEN LIFE TECHNOLOGIES) 1.5 mM, probe 3'-XbaI hu-C kappa and probe 5'-XhoI hu-C kappa 500 μM.

The amplification was carried out in an MJ-research PTC 200 thermal cycler (PELTIER THERMAL CYCLER) under the following conditions: 5 minutes at 94° C., then for the next 35 cycles 30 seconds at 94° C., 45 seconds at 55° C. and 1 minute at 72° C.

After checking the PCR products by 1% agarose gel electrophoresis analysis, the hu-C kappa cDNA is purified using the QIAquick Gel Extraction kit (QIAGEN) according to the supplier's directions.

4. Construction of the Expression Vector of the Light Chain of the Artificially Modified Antibody KM 60C3: pcDNA3® KM60C3-L (a). Digestion of the Vector pcDNA3® 60C3 L-VL and Hu-C Kappa cDNA, and Dephosphorylation of the Digested Vector The digestion is carried out under the following conditions: buffer NEB2 10× (5 μL), BSA 100× (0.5 μL), vector pcDNA3® 60C3 L-VL or hu-C kappa cDNA (1 μg), restriction enzyme XhoI (10U), restriction enzyme XbaI (10U). The restriction enzymes, the reaction buffer solutions and the BSA solution were supplied BY NEW ENGLAND BIOLABS Inc. The reaction is continued for 3 hours in a water-bath at 37° C. The digested vector and insert are purified using a QIAquick® Gel Extraction kit (QIAGEN) according to the supplier's directions. The vector is then dephosphorylated with CIP (NEW ENGLAND BIOLABS Inc.) for 1 hour at 37° c. The composition of the reaction medium is the following: buffer NEB3 10× (5 µL), vector (1 µg), CIP (1 µL).

(b). Ligation Reaction

The ligation provides insertion of the digested cDNA hu-C kappa cDNA in the digested and dephosphorylated vector pcDNA3® 60C3 L-VL by using T4 ligase (NEW ENGLAND BIOLABS Inc.). The reaction is carried out further in a water-bath at 16° C. for 16 hours in the following reaction medium: ligation buffer solution 5× (4 µL) (NEW ENGLAND BIOLABS Inc.), digested dephosphorylated vector 200 ng, T4 ligase (400U) (NEW ENGLAND BIOLABS Inc.), purified cDNA 170 ng (for a 1 kb insert). The insert:vector molar ratio is 3:1. The ligation reaction product is used for transforming competent bacteria *E. coli* XL1 blue (STRATAGENE).

(c). Checking for the Presence of the Insert Hu-Ckappa in the Vector pcDNA3® 60C3 L-VL by PCR The isolated resistant colonies are placed under sterile conditions in an extractor hood into a tube containing the PCR reaction mixture: dNTP (PROMEGA) 500 µM, Taq polymerase (INVITROGEN LIFE TECHNOLOGIES) 1 µL, PCR buffer solution (INVITROGEN LIFE TECHNOLOGIES) 10 µL, cDNA (matrix) 1 µL, $MgCl_2$ (INVITROGEN LIFE TECHNOLOGIES) 1.5 mM, probe 3'-XbaI hu-C kappa and probe 5'-XhoI hu-C kappa 500 µM. The amplification was carried out in an MJ-research PTC 200 thermal cycler under the following conditions: 5 minutes at 94° C., then for the next 35 cycles 30 seconds at 94° C., 45 seconds at 55° C. and 1 minute at 72° C. The size of the amplified PCR product is checked with 1% agarose gel electrophoresis analysis. Only those clones which were properly transformed give a PCR product having the expected size.

(d). Production of the Plasmid of Interest pcDNA3® KM60C3-L

A sterile tooth-pick is used, and after sampling the colony, is added to 5 mL of LB selective liquid medium containing 100 µg/mL ampicillin (SIGMA CHEMICALS CO) and 12.5 µg/mL tetracycline (SIGMA CHEMICALS CO), and incubated for 16 hours at 37° C. The bacterial dilution is then used for carrying out a plasmid DNA minipreparation using the QIAprep spin miniprep kit (QIAGEN) according to the supplier's directions.

5. Construction of the Expression Vector of the Light Chain of the Artificially Modified Antibody KM 8B6: pcDNA3® 8B6-L (a). Obtaining the Vector pcDNA3® Hu-C Kappa The vector pcDNA3® hu-C kappa was prepared from the vector pcDNA3® KM60C3-L by digestion using the restriction enzymes BamHI and XhoI. The composition of the reaction medium is the following: buffer NEB2 10× (5 µL), BSA 100× (0.5 µL), vector (1 µg), restriction enzyme BamHI (10U), restriction enzyme XhoI (10U). The restriction enzymes, the reaction buffer solutions and the BSA solution were supplied by NEW ENGLAND BIOLABS Inc. The reaction is continued for 3 hours in a water-bath at 37° C. The digested vector is purified using a QIAquick® Gel Extraction kit (QIAGEN) according to the supplier's directions. The vector is then dephosphorylated with CIP (NEW ENGLAND BIOLABS Inc.) for 1 hour at 37° C. The composition of the reaction medium is the following: buffer NEB3 10× (5 µL), vector (1 µg), CIP (1 µL).

(b). Extraction of Total RNA from 8B6 Hybridoma, Producing the 8B6 Monoclonal Antibody.

The total RNA is extracted from 106 8B6 hybridoma cells in exponential growth phase with the use of RNAble reagent (EUROBIO, Courtaboeuf, France) according to the supplier's directions. The total RNA concentration is determined by measuring the optical density at 260 nm (c). Obtaining the Nucleotide cDNA Sequence 8B6 L-VL Gene amplification of the cDNA coding for the variable region 8B6 L-VL was obtained from the messenger RNAs by RACE-PCR to provide the nucleotide sequence coding for the signal peptide (L) combined with its variable region (VL). This amplification was carried out using the SMART™ RACE cDNA Amplification kit obtained from the company BD BIOSCIENCES (San Jose, Calif., USA) according to the supplier's directions. The amount of total RNA used for the back-transcription is 1 µg. The reaction product was diluted in 100 µL of tricine EDTA buffer solution available from the supplier. A 2.5 µL volume of the diluted product was used for gene amplification. The antisense probe specific to the 8B6 VL cDNA used is as follows: 3'-mu C kappa 5'-gtt cat act cgt cct tgg tca acg tga ggg-3' which hybridates at the cDNA coding for the constant domain mu C-kappa of the kappa type mouse antibody light chain. The amplification was carried out by incubating the reaction mixture in a PERKIN-ELMER (PE) DNA thermal Cycler 480 (PERKIN ELMER WELLESLEY, Mass., USA) under the following conditions: 5 cycles (94° C. for 5 seconds, 72° C. for 3 minutes), followed by 5 cycles (94° C. for 5 seconds then 70° C. for 10 seconds followed by 3 minutes at 72° C.), and 25 cycles (94° C. for 5 seconds followed by 69° C. for 10 seconds and 3 minutes at 72° C.). The RACE-PCR reaction product is analyzed by 1% agarose gel electrophoresis (Q. BIOGENE, Morgan Irvine, Calif., USA) in a migration buffer solution of Tris EDTA pH 8 (40 mM Tris-base (SIGMA CHEMICALS CO), 25 mM EDTA (INERCHIM, Montluçon, France), 20 mM acetic acid (CARLO ERBA REAGENTI SPA, Rodano, MI, Italy). The products having the expected molecular weight are then purified by means of a QIAquick Gel Extraction kit (QIAGEN) according to the supplier's directions. The determination of the nucleic acid sequence of the resulting purified products was carried out by the company GENOME EXPRESS (Meylan, France) in order to check for the cDNA sequence coding for the 8B6 L-VL region. The sequence corresponding to the signal peptide combined with the light chain variable region of the 8B6 antibody was thus determined, and probes were designed for cloning 8B6 L-VL cDNA in the expression vector.

(d). Amplification of 8B6 L-VL cDNA

The amplification of 8B6 L-VL cDNA was achieved by RT-PCR from a total RNA extract from 60C3 hybridoma cells. The reaction mixture is the following: Oligo d(T)18 0.5 µg (NEW ENGLAND BIOLABS INC. Beverly, Mass., USA), RNA 1 µg, dNTP 0.5 mM (PROMEGA, Madison, Wis., USA), sterile water qsp 12 µL. This mixture is incubated for 5 minutes at 65° C. (dry regulated bath) then for 2 minutes at 4° C. (melting ice) to denaturate the RNA. To the reaction mixture, 4 µL of 5× First-strand Buffer solution (INVITROGEN LIFE BIOTECHNOLOGIES), 10 mM DTT (INVITROGEN LIFE BIOTECHNOLOGIES), 160 U of Rnasine (PROMEGA) and 800 U of reverse transcriptase (INVITROGEN LIFE BIOTECHNOLOGIES) are then added. The resulting mixture is incubated for 1 hour at 37° C. then at 70° C. for 15 minutes in order to stop the reaction. Copies of 8B6 L-VL cDNA are obtained by PCR gene amplification using the following synthetic oligonucleotides: 5'-BamHI 8B6 L-VL: 5'-AAG GGA TCC GCC ACC ATG AAG TTG CCT GTT-3' (sense probe, SEQ ID NO:14) and 3'-XhoI 8B6 L-VL: 5'-CCG TTT TAT CTC GAG CTT GGT CCC-3' (antisense probe, SEQ ID NO:15).

The synthetic probes used introduce silent mutations into the DNA sequence that do not result in a change to the amino acid sequence while creating BamHI and XhoI restriction sites required for cloning in the vector.

The reaction medium has the following composition: dNTP (PROMEGA) 500 µM, Taq polymerase (INVITROGEN LIFE TECHNOLOGIES) 1 µL, PCR buffer solution (INVITROGEN LIFE TECHNOLOGIES) 10 µL, cDNA (matrix) 1 µL, MgCl$_2$ (INVITROGEN LIFE TECHNOLOGIES) 1.5 mM, probe 3'-XhoI 8B6 L-VL and probe: 5'-BamHI 8B6 L-VL 500 µM.

The amplification was carried out in an MJ-research PTC 200 thermal cycler (PELTIER THERMAL CYCLER) under the following conditions: 5 minutes at 94° C., then for the next 35 cycles 30 seconds at 94° C., 45 seconds at 55° C. and 1 minute at 72° C.

After checking the PCR products by 1% agarose gel electrophoresis analysis, the 8B6 L-VL cDNA is purified using the QIAquick® Gel Extraction kit (QIAGEN) according to the supplier's directions.

(e). Digestion of 8B6 L-VL cDNA

The 8B6 L-VL cDNA is digested using the restriction enzymes BamHI and XhoI. The composition of the reaction medium is the following: buffer NEB2 10× (5 µL), BSA 100× (0.5 µL), 8B6 L-VL cDNA (1 µg), restriction enzyme BamHI (10U), restriction enzyme XhoI (10U). The restriction enzymes, the reaction buffer solutions and the BSA solution were supplied by NEW ENGLAND BIOLABS Inc. The reaction is continued for 3 hours in a water-bath at 37° C. The insert digested is purified using a QIAquick® Gel Extraction kit (QIAGEN) according to the supplier's directions.

(f). Ligation Reaction

The ligation provides insertion of the digested 8B6 L-VL cDNA in the digested and dephosphorylated vector pcDNA3® hu-C kappa by using T4 ligase (NEW ENGLAND BIOLABS Inc.). The reaction is carried out further in a water-bath at 16° C. for 16 hours in the following reaction medium: ligation buffer solution 5× (4 µL) (NEW ENGLAND BIOLABS Inc.), digested and dephosphorylated vector pcDNA3® hu-C kappa 200 ng, T4 ligase (400U) (NEW ENGLAND BIOLABS Inc.), purified 8B6 L-VL cDNA 170 ng (for a 1 kb insert). The insert:vector molar ratio is 3:1. The ligation reaction product is used for transforming competent bacteria *E. coli* XL1 blue (STRATAGENE).

(g). Checking for the Presence of the Insert 8B6 L-VL in the Vector pcDNA3® Hu-C Kappa by PCR The isolated resistant colonies are placed under sterile conditions in an extractor hood into a tube containing the PCR reaction mixture: dNTP (PROMEGA) 500 µM, Taq polymerase (INVITROGEN LIFE TECHNOLOGIES) 1 µL, PCR buffer solution (Invitrogen Life Technologies) 10 µL, cDNA (matrix) 1 µL, MgCl$_2$ (INVITROGEN LIFE TECHNOLOGIES) 1.5 mM, probe 3'-XhoI 8B6 L-VL and probe 5'-BamHI 8B6 L-VL 500 µM. The amplification was carried out in an MJ-research PTC 200 thermal cycler under the following conditions: 5 minutes at 94° C., then for the next 35 cycles 30 seconds at 94° C., 45 seconds at 55° C. and 1 minute at 72° C. The size of the amplified PCR product is checked with 1% agarose gel electrophoresis analysis. Only those clones which were properly transformed give a PCR product having the expected size.

(h). Production of the Plasmid of Interest pcDNA3® KM8B6 L

A sterile tooth-pick is used, and after sampling the colony, is added to 5 mL of LB selective liquid medium containing 100 µg/mL ampicillin (SIGMA CHEMICALS CO) and 12.5 µg/mL tetracycline (SIGMA CHEMICALS CO), and incubated for 16 hours at 37° C. The bacterial dilution is then used for carrying out a plasmid DNA minipreparation using the QIAprep® spin miniprep kit (QIAGEN) according to the supplier's directions.

6. Preparation of the cDNA Coding for the L-VH Variable Region of Mouse 60C3 Monoclonal Antibody (a). Obtaining the Nucleotide Sequence of 60C3 L-VH cDNA Gene amplification of the cDNA coding for the 60C3 L-VH variable region was obtained from the messenger RNAs by RACE-PCR to provide the nucleotide sequence coding for the signal peptide (L) combined with its variable region (VL). This amplification was carried out using the SMART™ RACE cDNA Amplification kit obtained from the company BD BIOSCIENCES (San Jose, Calif., USA) according to the supplier's directions. The amount of total RNA used for the back-transcription is 1 µg. The reaction product was diluted in 100 µL of tricine EDTA buffer solution available from the supplier. A 2.5 µL volume of the diluted product was used for gene amplification. The antisense probe specific to the 60C3VH cDNA used is as follows: 3'-60C3 L-VH 5'-TGC AGA GAC AGT GAC CAG CAG AGT AGT CCC-3' (antisense probe, SEQ ID NO:16) which hybridates at the cDNA coding for the mu C-kappa constant domain of the kappa type mouse antibody light chain. The amplification was carried out by incubating the reaction mixture in a Perkin-Elmer (PE) DNA thermal Cycler 480 (PERKIN ELMER WELLESLEY, Mass., USA) under the following conditions: 5 cycles (94° C. for 5 seconds, 72° C. for 3 minutes), followed by 5 cycles (94° C. for 5 seconds then 70° C. for 10 seconds followed by 3 minutes at 72° C.), and 25 cycles (94° C. for 5 seconds followed by 69° C. for 10 seconds and 3 minutes at 72° C.). The RACE-PCR reaction product is analyzed by 1% agarose gel electrophoresis (Q. BIOGENE, Morgan Irvine, Calif., USA) in a migration buffer solution of Tris EDTA pH 8 (40 mM Tris-base (SIGMA CHEMICALS Co), 25 mM EDTA (INERCHIM, Montlucon, France), 20 mM acetic acid (CARLO ERBA REAGENTI SPA, Rodano, MI, Italy). The products having the expected molecular weight are then purified by means of a QIAquick® Gel Extraction kit (QIAGEN) according to the supplier's directions. The determination of the nucleic acid sequence of the resulting purified products was carried out by the company GENOME EXPRESS (Meylan, France) in order to check for the cDNA sequence coding for the 60C3 L-VH region. The sequence corresponding to the signal peptide combined with the light chain variable region of the 60C3 antibody was thus determined, and probes were designed for cloning the 60C3 L-VH cDNA in the expression vector.

(b). Amplification of 60C3 L-VH cDNA

The amplification of 60C3 L-VH cDNA was achieved by RT-PCR from a total RNA extract from 60C3 hybridoma cells. The reaction mixture is the following: Oligo d(T)18 0.5 µg (NEW ENGLAND BIOLABS Inc. Beverly, Mass., USA), RNA 1 µg, dNTP 0.5 mM (PROMEGA, Madison, Wis., USA), sterile water qsp 12 µL. This mixture is incubated for 5 minutes at 65° C. (dry regulated bath) then 2 minutes at 4° C. (melting ice) to denaturate the RNA. To the reaction mixture, 4 µL of 5× First-strand Buffer solution (INVITROGEN LIFE BIOTECHNOLOGIES), 10 mM DTT (INVITROGEN LIFE BIOTECHNOLOGIES), 160 U of Rnasine (Promega) and 800 U of reverse transcriptase (INVITROGEN LIFE BIOTECHNOLOGIES) are then added. The resulting mixture is incubated for 1 hour at 37° C. then at 70° C. for 15 minutes in order to stop the reaction. Copies of 60C3 L-VH cDNA are obtained by PCR gene amplification using the following synthetic oligonucleotides: 5'-BamHI 60C3 L-VH:

5'-CAG GAT CCG AAC ACA CTG ACT CTA ACC ATG G-3' (sense probe, SEQ ID NO:17) and 3'-NheI 60C3 L-VH: 5'-T GCT AGC TGC AGA GAC AGT GAC CAG AGT-3' (antisense probe, SEQ ID NO:18).

The synthetic probes used introduce silent mutations into the DNA sequence that do not result in a change to the amino acid sequence while creating BamHI and XhoI restriction sites required for cloning in the vector.

The reaction medium has the following composition: dNTP (PROMEGA) 500 µM, Taq polymerase (Invitrogen Life Technologies) 1 µL, PCR buffer solution (INVITROGEN LIFE TECHNOLOGIES) 10 µL, cDNA (matrix) 1 µL, MgCl$_2$ (INVITROGEN LIFE TECHNOLOGIES) 1.5 mM, probe 3'-NheI 60C3 L-VH and probe 5'-BamHI 60C3 L-VH 500 µM.

The amplification was carried out in an MJ-research PTC 200 thermal cycler (PELTIER THERMAL CYCLER) under the following conditions: 5 minutes at 94° C., then for the next 35 cycles 30 seconds at 94° C., 45 seconds at 55° C. and 1 minute at 72° C.

After checking the PCR products by 1% agarose gel electrophoresis analysis, the 60C3 L-VH cDNA is purified using the QIAquick® Gel Extraction kit (QIAGEN) according to the supplier's directions.

7. Construction of the Recombinant Plasmid Having 60C3 L-VH Cdna (a). Construction of the Cloning Vector pBluescript II SK (+) 60C3 L-VH Inserting the sequence coding for the 60C3 L-VH region in the vector pBluescript II SK (+) comprises digestion of the latter by the restriction enzyme EcoRV (NEW ENGLAND BIOLABS Inc.) causing a blunt end cut. Treatment of the resulting linearized plasmid with Taq polymerase in the presence of dTTP provides further addition of a thymidine to the 3' end of the vector and prevents self-ligation. The Taq DNA polymerase used for obtaining the 60C3 L-VH cDNA has a 5'-3' exonuclease activity adding one terminal adenine to each 3' end of the PCR products which can be directly cloned in such vector. The yield of the ligation reaction is greatly enhanced due to A/T complementarity compared with the blunt end ligation reaction. The ligation reaction product is used for transforming competent bacteria E. coli XL1 blue (STRATAGENE).

(b). Checking for the Presence of the 60C3 L-VH Insert in the Vector pBluescript II SK (+) by PCR The isolated resistant colonies are placed under sterile conditions in an extractor hood into a tube containing the PCR reaction mixture: dNTP 500 µM (PROMEGA), Taq polymerase (INVITROGEN LIFE TECHNOLOGIES) 1 µL, PCR buffer solution (INVITROGEN LIFE TECHNOLOGIES) 10 µL, MgCl$_2$ (INVITROGEN LIFE TECHNOLOGIES) 1.5 mM, probe 3'-NheI 60C3 L-VH and probe 5'-BatnHI 60C3 L-VH 500 µM. The amplification was carried out in an MJ-research PTC 200 thermal cycler under the following conditions: 5 minutes at 94° C., then for the next 35 cycles 30 seconds at 94° C., 45 seconds at 55° C. and 1 minute at 72° C. The size of the amplified PCR product is checked with 1% agarose gel electrophoresis analysis. Only those clones which were properly transformed give a PCR product having the expected size.

(c). Production of the Plasmid of Interest pBluescript II SK (+) 60C3 L-VH

For this purpose, a sterile tooth-pick is used, and after sampling the colony, is added to 5 mL of LB selective liquid medium containing 100 µg/mL ampicillin (SIGMA CHEMICALS Co) and 12.5 µg/mL tetracycline (SIGMA CHEMICALS Co), and incubated for 16 hours at 37° C. The bacterial dilution is then used for carrying out a plasmid DNA mini-preparation using the QIAprep spin miniprep kit (QIAGEN) according to the supplier's directions.

(d). Checking for the Orientation of the 60C3 L-VH Insert in the Vector pBluescript II SK (+) 60C3 L-VH by Enzyme Digestion The presence of the 60C3 L-VH insert in the sense orientation is confirmed by enzyme digestion of the vector pBluescript II SK (+) 60C3 L-VH with the enzyme BamHI (NEW ENGLAND BIOLABS Inc.) according to the supplier's directions. In fact, the T cloning technique does not command one orientation for the insert which can therefore be inserted in the sense or antisense orientation. The 60C3 L-VH insert is only flanked by two restriction sites BamHI when it is in the sense orientation. Thus after digestion by the enzyme BamHI, the electrophoresis analysis makes it possible to distinguish and to select a clone having the 60C3 L-VH cDNA in the sense orientation.

8. Preparation of the cDNA Coding for the Constant Region of a Hu-C Gamma 1 Human Antibody a. Extraction of Total RNA from the Line of LP1 Human Myeloma Producing a Heavy Chain of Gamma 1 Isotype.

The total RNA is extracted from 106 LP1 hybridoma cells in exponential growth phase with the use of a RNAble reagent (EUROBIO, Courtaboeuf, France) according to the supplier's directions. The total RNA concentration is determined by measuring the optical density at 260 nm b. Gene Amplification of the Hu-C Gamma 1 cDNA Segment The amplification of the hu-C gamma 1 cDNA was carried out from a total RNA extract from LP1 hybridoma. The reaction mixture is the following: Oligo d(T)18 0.5 µg (NEW ENGLAND BIOLABS Inc. Beverly, Mass., USA), RNA 1 µg, dNTP 0.5 mM (PROMEGA, Madison, Wis., USA), sterile water qsp 12 µL. This mixture is incubated for 5 minutes at 65° C. (dry regulated bath) then 2 minutes at 4° C. (melting ice) to denaturate the RNA. To the reaction mixture, 4 µL of 5× First-strand Buffer solution (Invitrogen Life Biotechnologies), 10 mM DTT (Invitrogen Life Biotechnologies), 160 U of Rnasine (PROMEGA) and 800 U of reverse transcriptase (Invitrogen Life Biotechnologies) are then added. The resulting mixture is incubated for 1 hour at 37° C. then at 70° C. for 15 minutes in order to stop the reaction. Copies of hu-C gamma 1 cDNA are obtained by PCR gene amplification using the following synthetic oligonucleotides: 5'-NheI hu-C gamma 1:5'-CA GCT AGC ACC AAG GGC CCA TCG GTC TTC C-3' (sense probe, SEQ ID NO:19) and 3'-XbaI hu-C gamma 1:5'-AGC CTC TCC CTG TCT CCG GGT AAA TAA TCT AGA CG-3' (antisense probe, SEQ ID NO:20).

The synthetic probes used introduce silent mutations into the DNA sequence that do not result in a change to the amino acid sequence while creating NheI and XbaI restriction sites required for cloning in the vector.

The reaction medium has the following composition: dNTP (PROMEGA) 500 µM, Taq polymerase (INVITROGEN LIFE TECHNOLOGIES) 1 µL, PCR buffer solution (INVITROGEN LIFE TECHNOLOGIES) 10 µL, cDNA (matrix) 1 µL, MgCl$_2$ (INVITROGEN LIFE TECHNOLOGIES) 1.5 mM, probe 3'-XbaI hu-C gamma 1 and probe 5'-NheI hu-C gamma 1500 µM.

The amplification was carried out in an MJ-research PTC 200 thermal cycler (PELTIER THERMAL CYCLER) under the following conditions: 5 minutes at 94° C., then for the next 35 cycles 30 seconds at 94° C., 45 seconds at 55° C. and 1 minute at 72° C.

After checking the PCR products by 1% agarose gel electrophoresis analysis, the hu-C gamma 1 cDNA is purified using the QIAquick® Gel Extraction kit (QIAGEN) according to the supplier's directions.

9. Construction of a Recombinant Plasmid Having the 60C3 L-VH cDNA Coupled to Hu-C Gamma 1 cDNA: pBluescript II SK (+) KM60C3 H (a). Digestion of the Vector pBluescript II SK (+) 60C3 L-VH and Hu-C Gamma 1 cDNA, and Dephosphorylation of the Digested Vector The digestion is carried out under the following conditions: NEB2 10× buffer (5 µL), BSA 100× (0.5 µL), vector pBluescript II SK (+) 60C3 L-VH or hu-C gamma 1 cDNA (1 µg), restriction enzyme NheI (10U), restriction enzyme XbaI (10U). The restriction enzymes, the reaction buffer solutions and the BSA solution were supplied by NEW ENGLAND BIOLABS Inc. The reaction is continued for 3 hours in a water-bath at 37° C. The digested vector and insert are purified using a QIAquick® Gel Extraction kit (QIAGEN) according to the supplier's directions. The vector is then dephosphorylated with CIP (NEW ENGLAND BIOLABS Inc.) for 1 hour at 37° c.

The composition of the reaction medium is the following: NEB3 10× buffer (5 µL), vector (1 µg), CIP (1 µL).

(b). Ligation Reaction

The ligation provides insertion of the digested hu-C gamma 1 cDNA in the digested and dephosphorylated vector pBluescript II SK (+) 60C3 L-VH by using T4 ligase (NEW ENGLAND BIOLABS Inc.). The ligation reaction is carried out further in a water-bath at 16° C. for 16 hours in the following reaction medium: ligation buffer solution 5× (4 µL) (NEW ENGLAND BIOLABS Inc.), digested dephosphorylated vector pBluescript II SK (+) 60C3 L-VH 200 ng, T4 ligase (400U) (NEW ENGLAND BIOLABS Inc.), purified hu-C gamma 1 cDNA 170 ng (for a 1 kb insert). The insert: vector molar ratio is 3:1. The ligation reaction product is used for transforming competent bacteria E. coli XL1 blue (STRATAGENE).

(c). Checking for the Presence and Orientation of the Hu-C Gamma 1 Insert in the Vector pBluescript II SK (+) 60C3 L-VH by PCR Because of the choice of the NheI and XbaI restriction sites, the hu-C gamma 1 insert can be in the sense or antisense orientation. This is because of the sequence of the restriction sites which does not command one orientation for the insert. The sense orientation of the insert is confirmed by PCR. Isolated colonies are placed under sterile conditions in an extractor hood respectively into a tube containing the PCR reaction mixture: dNTP 500 µM (PROMEGA), Taq polymerase (INVITROGEN LIFE TECHNOLOGIES) 1 µL, PCR buffer solution (INVITROGEN LIFE TECHNOLOGIES) 10 µL, MgCl$_2$ (INVITROGEN LIFE TECHNOLOGIES) 1.5 mM, sense probe and antisense probe 500 µM. The amplification was carried out in an MJ-research PTC 200 thermal cycler under the following conditions: 5 minutes at 94° C., then for the next 35 cycles 30 seconds at 94° C., 45 seconds at 55° C. and 1 minute at 72° C. The probes used are: 5'-BamHI 60C3 L-VH: 5'-CAG GAT CCG AAC ACA CTG ACT CTA ACC ATG G-3' (sense probe, SEQ ID NO:21) and 3'-XbaI hu-C gamma 1:5'-AGC CTC TCC CTG TCT CCG GGT AAA TAA TCT AGA CG-3' (antisense probe, SEQ ID NO:21).

If the insert is not in the proper orientation, the probes are found on the same strand of the sequence that is to be amplified, resulting in no amplification. The size of the amplified PCR product is checked with 1% agarose gel electrophoresis analysis. Only those clones which were properly transformed give a PCR product having the expected size.

(d). Production of the Plasmid of Interest pBluescript II SK (+) KM60C3 H

A sterile tooth-pick is used, and after sampling the colony, is added to 5 mL of LB selective liquid medium containing 100 µg/mL ampicillin (SIGMA CHEMICALS Co) and 12.5 µg/mL tetracycline (SIGMA CHEMICALS Co), and incubated for 16 hours at 37° C. The bacterial dilution is then used for carrying out a plasmid DNA minipreparation using the QIAprep® spin miniprep kit (QIAGEN) according to the supplier's directions.

10. Construction of the Expression Vector of the Artificially Modified Antibody Heavy Chain KM 8B6: pcDNA3/Hygro 8B6-H (a). Obtaining the Vector pBluescript II SK (+) Hu-C Gamma 1

The vector pBluescript II SK (+) hu-C gamma 1 was prepared from the vector pBluescript II SK (+) KM60C3 H by digestion using the restriction enzymes BamHI and XbaI. The composition of the reaction medium is the following: NEB2 10× buffer (5 µL), BSA 100× (0.5 µL), vector (1 µg), restriction enzyme BamHI (10U), restriction enzyme XbaI (10U). The restriction enzymes, the reaction buffer solutions and the BSA solution were supplied by NEW ENGLAND BIOLABS Inc. The reaction is continued for 3 hours in a water-bath at 37° C. The vector is then purified using a QIAquick Gel Extraction kit (QIAGEN) according to the supplier's directions. The vector is then dephosphorylated with CIP (NEW ENGLAND BIOLABS Inc.) for 1 hour at 37° C. The composition of the reaction medium is the following: NEB3 10× buffer (5 µL), vector (1 ng), CIP (1 µL).

(b). Extraction of Total RNA from 8B6 Hybridoma Producing the 8B6 Monoclonal Antibody.

The total RNA is extracted from 106 8B6 hybridoma cells in exponential growth phase with the use of RNAble reagent (EUROBIO, Courtaboeuf, France) according to the supplier's directions. The total RNA concentration is determined by measuring the optical density at 260 nm (c). Obtaining the Nucleotide cDNA Sequence 8B6 L-VH Gene amplification of the cDNA coding for the 8B6 L-VH variable region was obtained from the messenger RNAs by RACE-PCR to provide the nucleotide sequence coding for the signal peptide (L) combined with its variable region (VH). This amplification was carried out using the SMART RACE cDNA Amplification kit obtained from the company BD BIOSCIENCES (San Jose, Calif., USA) according to the supplier's directions. The amount of total RNA used for the back-transcription was 1 µg. The reaction product was diluted in 100 µL of tricine EDTA buffer solution available from the supplier. A 2.5 µL volume of the diluted product was used for gene amplification. The antisense probe specific to the 8B6 L-VH cDNA used is as follows: 3'-mu C gamma 3 5'-tGA TCA ACT CAG TCT TGC TGG CTG GGT GGG-3' (SEQ ID NO:23) which hybridates at the cDNA coding for the heavy chain mu C-gamma 3 constant domain of gamma 3 type mouse antibodies. The amplification was carried out by incubating the reaction mixture in a PERKIN-ELMER (PE) DNA thermal Cycler 480 (PERKIN ELMER WELLESLEY, Mass., USA) under the following conditions: 5 cycles (94° C. for 5 seconds, 72° C. for 3 minutes), followed by 5 cycles (94° C. for 5 seconds then 70° C. for 10 seconds followed by 3 minutes at 72° C.), and 25 cycles (94° C. for 5 seconds followed by 69° C. for 10 seconds and 3 minutes at 72° C.). The RACE-PCR reaction product is analyzed by 1% agarose gel electrophoresis (Q. Biogene, Morgan Irvine, Calif., USA) in a migration buffer solution of Tris EDTA pH 8 (40 mM Tris-base (SIGMA CHEMICALS Co), 25 mM EDTA (IN-ERCHIM, Montlucon, France), 20 mM acetic acid (CARLO ERBA REAGENTI SPA, Rodano, MI, Italy). The products having the expected molecular weight are then purified by means of a QIAquick® Gel Extraction kit (QIAGEN) according to the supplier's directions. The determination of the nucleic acid sequence of the resulting purified products was carried out by the company GENOME EXPRESS (Meylan, France) in order to check for the cDNA sequence coding for the 8B6 L-VH region. The sequence corresponding to the signal peptide combined with the heavy chain variable region of the 8B6 antibody was thus determined, and probes were designed for cloning the 8B6 L-VH cDNA in the expression vector pBluescript II SK (+) hu-C gamma 1.

(d). Gene Amplification of 8B6 L-VH Segments

The amplification of 8B6 L-VH cDNA was achieved by RT-PCR from a total RNA extract of 8B6 hybridoma cells. The reaction mixture is the following: Oligo d(T)18 1 μL (NEW ENGLAND BIOLABS Inc. Beverly, Mass., USA), RNA 1 μg, dNTP 0.5 mM (PROMEGA, Madison, Wis., USA), sterile water qsp 12 μL. This mixture is incubated for 5 minutes at 65° C. (dry regulated bath) then for 2 minutes at 4° C. (melting ice) to denaturate the RNA. To the reaction mixture, 4 μL of 5× First-strand Buffer solution (INVITROGEN LIFE BIOTECHNOLOGIES), 10 mM DTT (INVITROGEN LIFE BIOTECHNOLOGIES), 160 U of Rnasine (PROMEGA) and 800 U of reverse transcriptase (INVITROGEN LIFE BIOTECHNOLOGIES) are then added. The resulting mixture is incubated for 1 hour at 37° C. then at 70° C. for 15 minutes in order to stop the reaction. Copies of 8B6 L-VH cDNA are obtained by PCR gene amplification using the following synthetic oligonucleotides: 5'-BamHI 8B6 L-VH: 5'-CCG TCG GAT CCG GCC ACC ATG AAG TTG TGG-3' (sense probe, SEQ ID NO:24) and 3'-NheI 8B6 L-VH: 5'-CGG GGT GCT AGC TGA GGA GAC TGT-3' (antisense probe, SEQ ID NO:25).

The probes used introduce silent mutations into the DNA sequence that do not result in a change to the amino acid sequence while creating BamHI and NheI restriction sites required for cloning in the vector.

The reaction medium has the following composition: dNTP 500 μM (PROMEGA), Taq polymerase (INVITROGEN LIFE TECHNOLOGIES) 1 μL, PCR buffer solution (INVITROGEN LIFE TECHNOLOGIES) 10 μL, cDNA (matrix) 1 μL, MgCl$_2$ (INVITROGEN LIFE TECHNOLOGIES) 1.5 mM, probe 3'-NheI 8B6 L-VH and probe 5'-BamHI 8B6 L-VH 500 M.M.

The amplification was carried out in an MJ-research PTC 200 thermal cycler (PELTIER THERMAL CYCLER) under the following conditions: 5 minutes at 94° C., then for the next 35 cycles 30 seconds at 94° C., 45 seconds at 55° C., and 1 minute at 72° C.

After checking the PCR products by 1% agarose gel electrophoresis analysis, the 8B6 L-VH cDNA is purified using the QIAquick® Gel Extraction kit (QIAGEN) according to the supplier's directions.

(e). Digestion of 8B6 L-VH Cdna

The 8B6 L-VH cDNA is digested using the restriction enzymes BamHI and NheI. The composition of the reaction medium is the following: NEB2 10× buffer (5 HL), BSA 100× (0.5 μL), 8B6 L-VH cDNA (1 μg), restriction enzyme BamHI (10U), restriction enzyme NheI (10U). The restriction enzymes, the reaction buffer solutions and the BSA solution were supplied by NEW ENGLAND BIOLABS Inc. The reaction is continued for 3 hours in a water-bath at 37° C. The insert digested is purified using a QIAquick® Gel Extraction kit (QIAGEN) according to the supplier's directions.

(f). Ligation Reaction

The ligation provides insertion of the digested 8B6 L-VH cDNA in the digested and dephosphorylated vector pBluescript II SK (+) hu-C gamma 1. The reaction is carried out further in a water-bath at 16° C. for 16 hours in the following reaction medium: ligation buffer solution 5× (4 μL) (NEW ENGLAND BIOLABS Inc.), digested dephosphorylated vector pBluescript II SK (+) hu-C gamma 1 200 ng, T4 ligase (400U) (NEW ENGLAND BIOLABS Inc.), purified 8B6 L-VH cDNA 170 ng (for a 1 kb insert). The insert:vector molar ratio is 3:1. The ligation reaction product is used for transforming competent bacteria E. coli XL1 blue (STRATAGENE).

(g). Obtaining cDNA Coding for the Artificially Modified Antibody Heavy Chain

The vector pBluescript II SK (+) KM8B6 H is digested by restriction enzymes BamHI and XbaI for producing the cDNA coding for the artificially modified antibody heavy chain. The composition of the reaction medium is the following: NEB2 10× buffer (5 μL), BSA 100× (0.5 μL), vector (1 μg), restriction enzyme BamHI (10U), restriction enzyme XbaI (10U). The restriction enzymes, the reaction buffer solutions and the BSA solution were supplied by NEW ENGLAND BIOLABS Inc. The reaction is continued for 3 hours in a water-bath at 37° C. The released insert is purified using a QIAquick® Gel Extraction kit (QIAGEN) according to the supplier's directions.

(h). Digestion of the Vector pcDNA3/Hygro and Dephosphorylation of the Digested Vector The digestion is carried out under the following conditions: NEB2 10× buffer (5 μL), BSA 100× (0.5 J μL), vector (1 μg), restriction enzyme BamHI (10U), restriction enzyme XbaI (10U). The restriction enzymes, the reaction buffer solutions and the BSA solution were supplied by NEW ENGLAND BIOLABS Inc. The reaction is continued for 3 hours in a water-bath at 37° C. The digested vector and insert are purified using a QIAquick® Gel Extraction kit (QIAGEN) according to the supplier's directions. The vector is then dephosphorylated with CIP (NEW ENGLAND BIOLABS Inc.) for 1 hour at 37° c. The composition of the reaction medium is the following: NEB3 10× buffer (5 nL), vector (1 μg), CIP (1 μL).

(i). Ligation Reaction

The ligation reaction provides insertion of the cDNA coding for the artificially modified antibody heavy chain in the digested and dephosphorylated vector pcDNA3/Hygro. The ligation reaction is carried out further in a water-bath at 16° C. for 16 hours in the following reaction medium: ligation buffer solution 5× (4 μL) (NEW ENGLAND BIOLABS Inc.), digested dephosphorylated vector pcDNA3/Hygro 200 ng, T4 ligase (400U) (NEW ENGLAND BIOLABS Inc.), the purified cDNA coding for the artificially modified antibody heavy chain 170 ng (for a 1 kb insert). The insert:vector molar ratio is 3:1. The ligation reaction product is used for transforming competent bacteria E. coli XL1 blue (STRATAGENE).

(j). Checking for the Presence of cDNA Coding for the Artificially Modified Antibody Heavy Chain in the Vector pcDNA3/Hygro by PCR The isolated resistant colonies are placed under sterile conditions in an extractor hood into a tube containing the PCR reaction mixture: dNTP 500 μM (PROMEGA), Taq polymerase (INVITROGEN LIFE TECHNOLOGIES) 1 μL, PCR buffer solution (INVITROGEN LIFE TECHNOLOGIES) 10 μL, MgCl$_2$ (INVITROGEN LIFE TECHNOLOGIES) 1.5 mM, probe 3' and probe 5' 500 μM. The amplification was carried out in an MJ-research PTC 200 thermal cycler under the following conditions: 5 minutes at 94° C., then for the next 35 cycles 30 seconds at 94° C., 45 seconds at 55° C. and 1 minute at 72° C. The probes used are: 5'-BamHI 60C3 L-VH: 5'-CCG TCG GAT CCG GCC ACC ATG AAG TTG TGG-3' (sense probe, SEQ ID NO:26) and 3'-NheI 8B6 L-VH: 5'-CGG GGT GCT AGC TGA GGA GAC TGT-3' (antisense probe, SEQ ID NO:27).

The size of the amplified PCR product is checked with 1% agarose gel electrophoresis analysis. Only those clones which were properly transformed give a PCR product having the expected size.

(k). Production of the Plasmid of Interest pcDNA3 KM8B6 L

A sterile tooth-pick is used, and after sampling the colony, is added to 5 mL of LB selective liquid medium containing 100 µg/mL ampicillin (SIGMA CHEMICALS Co) and 12.5 µg/mL tetracycline (SIGMA CHEMICALS Co), and incubated for 16 hours at 37° C. The bacterial dilution is then used for carrying out a plasmid DNA minipreparation using the QIAprep® spin miniprep kit (QIAGEN) according to the supplier's directions.

Figure 4:
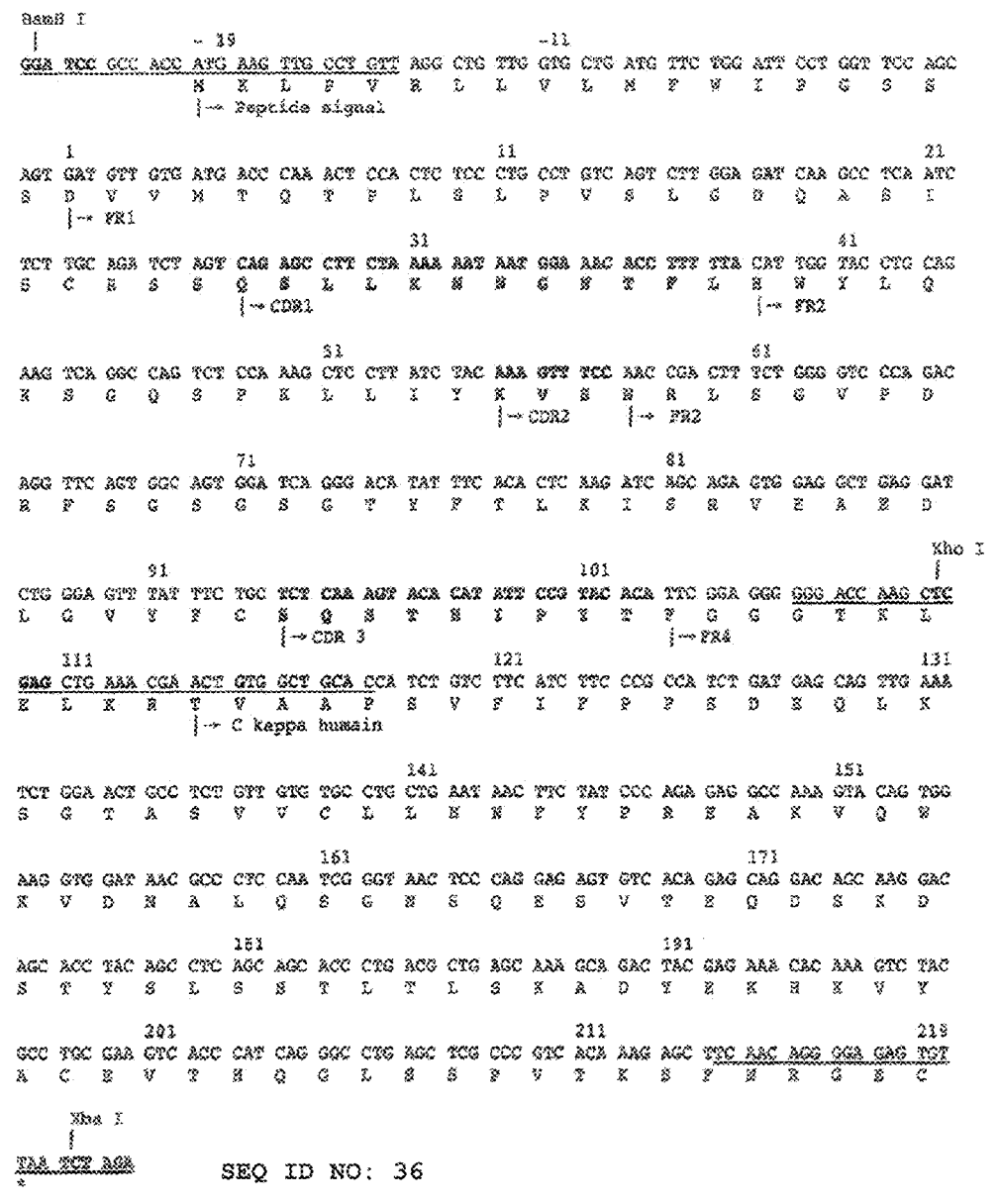
Figure 9:
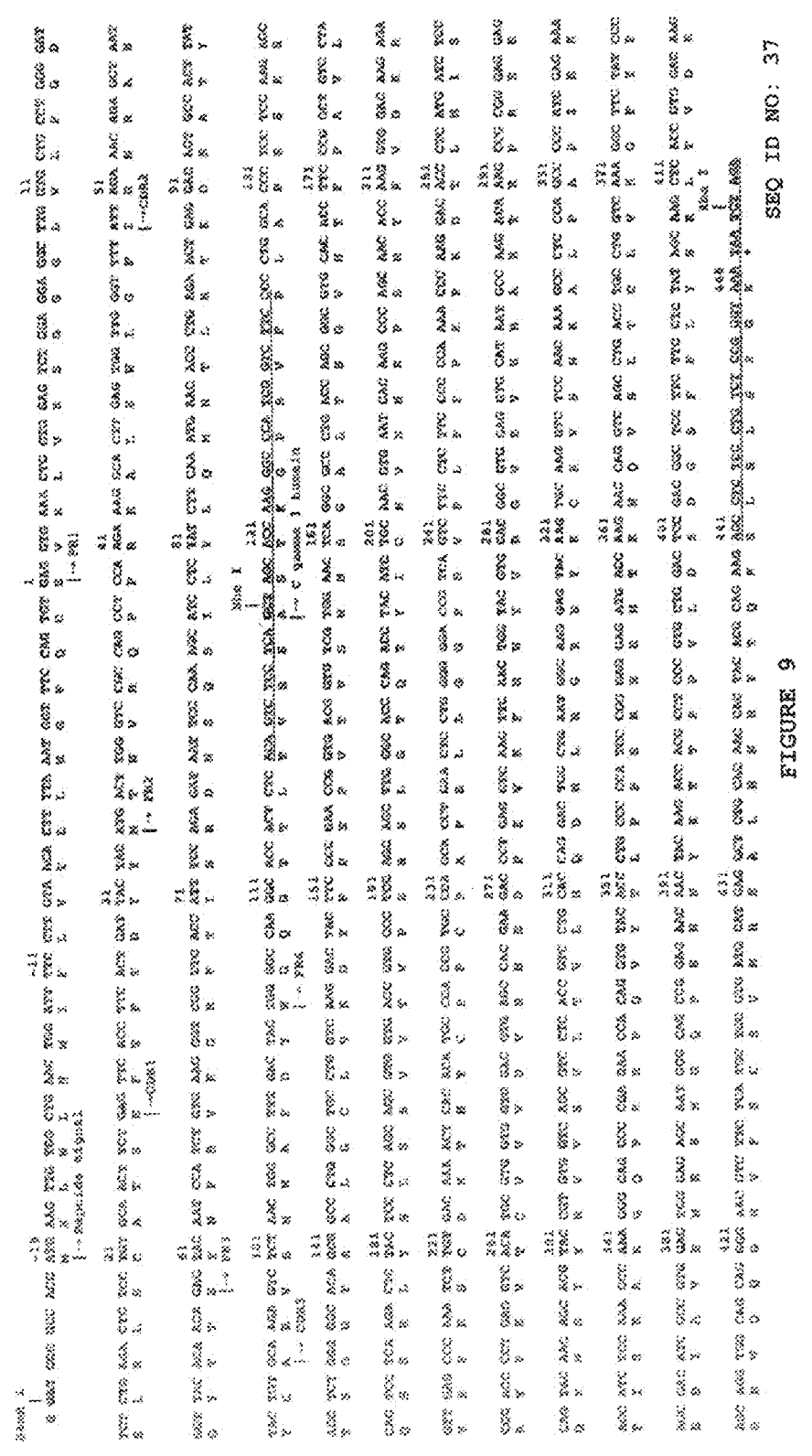

11. Transfection of CHO Cells for Expressing Artificially Modified KM8B6 Antibody CHO cells were used as host cells for expressing and secreting artificially modified KM8B6 antibody. These cells were co-transfected with the plasmids pDNA3® KM8B6-L and pDNA3.1/Hygro© KM8B6-H, coding respectively for the light chain (FIG. 4) and for the heavy chain (FIG. 9) of the artificially modified KM8B6 antibody, using PolyFect® kit (QIAGEN GMBH, Hildn, Germany) according to the supplier's directions. The cells transformed were selected for their resistance to Geneticin® and hygromycin B® (INVITROGEN LIFE TECHNOLOGIES, Carlsbad, Calif., USA). The resistant clones were obtained by a conventional cloning technique through limited dilution. They were then selected for their expression and their secretion of KM8B6 antibody with an ELISA immunoenzymatic assay. A stable transfectant clone secreting KM8B6 antibody at 3.8 ng/mL was selected.

12. Purification of 8B6 and KM8B6 Antibodies

The mouse monoclonal antibodies specific to gangliosides were produced from a corresponding hybridoma culture supernatant (Cerato et al, 1997). They were purified by protein A chromatography (GE HEALTHCARE AMERSHAM BIOSCIENCE AB, Uppsala, Sweden) according to a procedure developed by the inventor which limits the irreversible phenomena of homophilic aggregations of mouse IgG3 (Chapman et al, 1990). The column is first equilibrated with a buffer, 0.1 M Tris-HCl pH 7.6. A 2 L sample of culture supernatant containing 10% equilibration buffer is run through the column with a flow rate of 1 mL/min. The column is then washed with 10 volumes of equilibration buffer. The materiel fixed to protein A is eluted with an acidic buffer 0.1 M citrate, 0.3 M NaCl, pH 3 then collected by fractions immediately neutralized by previously introducing a buffer, 1M Tris-HCl, pH 7.6, in the collecting tubes. The progress of the purification is monitored by measuring the change in optical density of the collected fractions. The valuable fractions are then dialyzed in a PBS solution pH 7.4 NaCl 0.3M and sterilized by filtration over a 0.22 µm filter. The amount of protein is determined by measuring the optical density at 280 nm, then the mAb concentration is adjusted to a concentration lower than or equal to 0.9 mg AcN per mL so as to prevent the homophilic aggregation phenomenon of the mouse IgG3. The purified AcMs are stored as such at 4° C. before use.

The artificially modified KM8B6 antibody was purified by protein A affinity chromatography from the CHO cell culture supernatant derived from a stably co-transfected clone with the plasmids pcDNA3 KM8B6-L and pcDNA3/Hygro KM8B6-H.

The purified antibodies are analyzed by SDS-PAGE analysis under reducing denaturing conditions. The samples are taken up in a buffer solution Tris-HCl 0.5 M pH 6.8, containing 10% glycerol (VWR, Fontenay sous Bois, France) and 5% β-mercaptoethanol (PROMEGA). They are boiled for 5 minutes, then analyzed by SDS-PAGE electrophoresis according to the Laemmli method. The proteins are placed in an amount of 3 µg in wells made of 1 5 mm thick polyacrylamide gel with polyacrylamide concentrations for upper and lower gel of 4.5% and 12%, respectively (VWR). After electrophoresis at 200V for 45 minutes at room temperature, the gel is fixed and stained with Coomassie blue R250 (SIGMA CHEMICALS Co). The molecular weights are calculated from the migration of molecular weight markers, Precision Plus Protein® Standards (BIO-RAD).

The 12% SDS-PAGE gel analysis under reducing denaturing conditions shows that the molecular weights of the L and H chimeric chains are 25 kDa and 50 kDa respectively. The 6% SDS-PAGE gel analysis under non-reducing denaturating conditions shows that the L and H chains are properly assembled to produce an antibody molecule and that the molecular weight of the artificially modified antibody is approximately 150 kDa.

13. Study of the KM8B6 Antibody Specificity (a). By Indirect Immunofluorescence on Living Cells The antibody specificity was examined on IMR32 cells expressing O-acetylated GD2 and on Neuro 2A cells not expressing O-acetylated GD2. $10^6$ cells are incubated with 8B6 or KM8B6 antibody for 30 minutes at 4° C. The cells are then washed twice in 1% PBS-BSA buffer pH 7.4 and incubated again for 30 minutes in the presence of goat F(ab)2 anti-mouse immunoglobulin or anti-human immunoglobulin antibodies labeled with fluorescein isothiocyanate (JACKSON IMMUNORESEARCH EUROPE LTD, Cambrideshire, UK) at a 1/100 dilution in 1% PBS-BSA. After washing again three times in PBS, 10 000 cells are analyzed using a flow cytometer FACScan (Beton-Dockinson, Mountain View, Calif.) in a SSC/FL1-H window after removal of dead cells and cell debris. Cells having a fluorescence higher than 1 Log after adjusting the base using controls non-specifically labeled by the second antibodies alone, are said to be positive.

The results obtained show that KM8B6 antibody, like 8B6 antibody, only recognizes IMR-32 cells.

(b). By ELISA Immunoenzymatic Assay on Desiccated Cells in a 96-Well Microtitration Plate The antibody specificity was examined on IMR-32 cells expressing O-acetylated GD2 and on Neuro 2A cells not expressing O-acetylated GD2. In vitro cultures of tumor cells are detached from their culture substrate by treatment with trypsin. After three washes with PBS, the cells are distributed in Maxisorp flat-bottom microtitration plates (NUNC A/S, Roskilde, Denmark) in an amount of $10^5$ cells per well in a 50 µL volume of PBS. The plates are then placed in an oven at 37° C. overnight to evaporate the PBS. The plates can be used directly or conserved for several months at room temperature before use. For analysis, the plates are first incubated under stirring for one hour at room temperature with 200 µL of a PBS buffer solution pH 7.4 containing 1% BSA in order to saturate the non-specific sites. The plate is then incubated for 2 hours under stirring at room temperature with 100 µL of an antibody solution diluted in PBS buffer with 0.1% BSA. After three washes, each time with 200 µL of PBS buffer, 100 µL of a solution of F(ab')2 from biotinylated antibodies specific either to total mouse immunoglobulins, or to total human immunoglobulins (JACKSON IMMUNORESEARCH EUROPE LTD, Cambrideshire, UK) diluted to 1/2500 in 0.1% PBS-BSA, is placed in each well. After incubation for 1 hour under stiffing at room temperature and three washes in PBS, a solution of biotinylated streptavidine peroxydase (JACKSON IMMUNORESEARCH EUROPE LTD, Cambrideshire, UK) in 0.1% PBS-BSA is reacted for 1 hour before being removed by washing. The development of the fixed complex is demonstrated by adding 100 µL of ABTS substrate (ROCHE DIAGNOSTICS GMBH MANNHEIM, Germany). The optical density is determined by reading the plate on a spectrophotometer (Multisan EX, Thermo Electron Corporation, Waltham, Mass.) at 405 nm at different time intervals.

The results obtained show that KM8B6 antibody, like 8B6 antibody, is fixed in a dose-dependent way exclusively on IMR-32 cells.

(c). On a Thin Layer of Silica

The analysis was carried out on a total ganglioside extract of IMR-32 cells. The tissue gangliosides are extracted according to the techniques described by Ariga et al. (1991). The sample to be extracted is ground in ten volumes of a chloroform/methanol (C:M) mixture (1:1, v/v) and left under mechanical stiffing at room temperature overnight. After filtration, the residue is taken up into 2.5 volumes of (C:M) (1:1, v/v) and stirring is resumed for another six hours. The mixture is then filtered and the two filtrates are evaporated under reduced pressure on a rotary evaporator. The dry residue is then placed on a column containing 2 mL of DEAE-Sephadex A-25 in acetate form (SIGMA CHEMICALS Co). The neutral lipids are removed by 15 mL of solvent A. The gangliosides are then eluted with 15 mL of methanol containing 0.4M of sodium acetate (SIGMA CHEMICALS Co). To the resulting fraction, 30 mL of PBS pH 7.4 are added for desalting on a Sep-Pak column (Waters Co., Milford, Mass., USA) of C18 hydrophobic gel according to McLuer's method (1990). The C18 gel is first conditioned with two column volumes of methanol followed by 1:2 (v/v) methanol/PBS mixture. The extract to be desalted is then run through the column at a rate of 1 mL/min. The hydrocarbon chains of the gangliosides interact through hydrophobic bonds with the gel whereas the salts and others non hydrophobic molecules are removed by two column volumes of distilled water. The glycosphingolipids are then eluted by a volume of methanol then a volume of a 2:1 (v/v) chloroform/methanol mixture. The gangliosides eluted from this column are concentrated in another suitable volume of a 2:1 (v/v) C/M mixture and stored at −20° C.

The gangliosides are then separated by thin layer chromatography. This method makes it possible to determine the profile of the total gangliosides. The HPTLC plates are comprised of silica gel 60 (MERCK) coated on an aluminum foil. The spotted gangliosides are left to migrate for 20 minutes at room temperature in a tank saturated with migration solvent. This solvent (mobile phase) is comprised of a $C/M/CaCl_2$ mixture at 0.22% in water (50:45:10, v/v/v). The more a ganglioside is sialylated, the more polar it is and the least mobile it will be. Gangliosides plate detection is carried out chemically with a resorcinol/HCl reagent (Svennerholm, 1963). This reagent only reacts with sialic acid which is characteristic of gangliosides. After development with resorcinol, several stained bands are observed corresponding to the migration of the gangliosides from the total extract. Identification of the gangliosides separated is carried out either by means of specific monoclonal antibodies, or by comparison with standard gangliosides used as markers having migrated at the same time as the ganglioside extract to be tested.

After migration of the gangliosides on a thin layer of silica, the plate is submerged into a 0.01% poly-(isobutyl)-methacrylate solution in hexane for 1 minute then dried in the air. This enables to plasticize the plate in order to prevent the gel from detaching from its substrate during subsequent stages. The ELISA assay procedure involving desiccated cells is then monitored except for the development of the bonding of the antibody to the ganglioside which is carried out with a 4-chloro-1-naphtol solution (SIGMA ALDRICH CHEMIE GMBH, STENHEIM, Germany) prepared just before use in an amount of 1 mg of product dissolved in 1 mL of methanol, taken up into 20 mL of PBS and added with 30 µL of 30 volume oxygenated water.

The results show that KM8B6 antibody, like 8B6 antibody, only recognizes O-acetylated GD2 in the absence of alkali treatment of the ganglioside extract.

14. Study of GD2 Ganglioside Distribution and its O-Acetylated Form in the Nervous System and on Tumor Tissues Tumor samples (glioblastoma, neuroblastoma, melanoma, lung cancer) were obtained from surgical resection. Samples of human peripheral nerves were collected from the distal sensory branch of the musculo-cutaneous nerve, the side branch of the peroneal nerve. These are samples for diagnosing peripheral neuropathy or anterior horn conditions (normal sensory nerves), which have caused diagnostic problems. A volume of no more than 0.5 $cm^3$ of tissues is sampled and frozen in isopentane cooled to liquid nitrogen temperature. After 60 seconds, the sample is removed and transferred into a freezing tube refrigerated beforehand to −70° C. 10 µM sections of frozen tissue are cut by means of a cryostat. The sections are recovered on Suoerfrost Gold+glass slides (VWR). The sections are dried in the air for 3 minutes then fixed in acetone for 10 minutes and dried again in the air. The sections are then stored at −20° C. until they are analyzed by an immunohistochemical method Immunostaining of the tissue samples was carried out using the following primary mouse mAb:

Primary antibodies specific to GD2:
mAb 10B8 (IgG3, kappa) specific to GD2
8B6 mAb (IgG3, kappa) specific to GD2-O—Ac
Primary antibodies used as a reagent for negative control: MCA2063 mAb (IgG3, kappa) specific to DNP (Serotec France, Cergy Saint Christophe, Rance).

The development of the bonding of these antibodies on the test tissue samples was carried out with a DakoCytomation Envision+System, Peroxydase HRP kit (DAKO, Glostrup, Denmark) for use with mouse primary antibodies according to the supplier's directions. The samples are then mounted between slides and cover-glasses with an aqueous mounting medium Aquadex (VWR). The labeling determination is then carried out by light microscopy analysis using a light microscope with a magnification of 100 and 400. Digital microphotographs of three microscope fields selected at random per sample analyzed.

All tumor samples, from various patients, showed a positive membrane and cytoplasm labeling with 10B8 and 8B6 antibodies, whereas sound cells were not labeled by any of these antibodies. No labeling was detected with MCA2063 anti-DNP antibody.

All the nerve samples tested showed a labeling at myelinated fiber internodes with 10B8 antibody, whereas axons and fibroblasts showed no labeling. This labeling is not found or is hardly detectable with 8B6 antibody. No labeling was observed with MCA2063 antibody.

15. Study of the Cytotoxicity of O-Acetylated 8B6 and KM8B6 Anti-GD2 Antibodies (a). Preparation of the Target Cell Suspension.

$1\times10^6$ cells of IMR32 human neuroblastoma cultured in RPMI medium are incubated in the presence of 1.85 MBq of $Na_2{}^{51}CrC_4$ for 1 hour at 37° C. The cells are then washed three times with RPMI and centrifuged before being resuspended in RPMI, and incubated at 4° C. for 30 minutes in order to measure the spontaneous salting-out of the radioactive substance.

After the last centrifugation, the cells are taken up into 5 mL of RPMI for adjusting the concentration at $2\times10^5$ cells/mL.

(b). Preparation of Effector Cells

Human blood was sampled from voluntary donors in blood test tubes containing heparin. Peripheral blood leukocytes were separated from the total blood on a Ficoll® gradient by centrifugation (1,800×g for 30 minutes). The resulting cells are centrifuged three times in RPMI at 1500×g for washing and resuspended in RPMI to give a cell concentration of $5\times10^6$ cells/mL.

(c). Measurement of ADCC Activity

In each of the wells of a 96-well microtitration plate with U-shaped bottom, obtained from the company Falcon, 50 μL of target cell suspension, obtained in a), are added. 100 μL of the effector cell suspension, obtained in b), are then added, i.e. 50 000 cells per well. The ratio of target cells to the number of effector cells is 1:50. 8B6 antibody, and artificially modified KM8B6 antibody, and Rituxan®, kappa IgG1, anti-CD20 human-mouse antibody, used as negative control, are then added to each well at a concentration of 1 μg/mL or 10 μg/mL. The mixture is incubated at 37° C. for 4 hours. After centrifugation, the plate is centrifuged and the amount of $^{51}Cr$ in the supernatant is measured using a ?-counter. The total amount of $^{51}Cr$ released is measured according to the same procedure by adding medium exempt from antibody, and a 5 N sodium hydroxide solution instead of the effector cell suspension. The ADCC is then calculated using the following formula:

% ADCC activity=($^{51}Cr$ in the supernatant–$^{51}Cr$ spontaneously released)/($^{51}Cr$ total–$^{51}Cr$ spontaneously released)

16. Tumor Activity of 8B6 Antibody in a Syngenic Model of Mouse Lymphoma.

The anti-tumor activity of 8B6 antibody was determined in the model of syngenic subcutaneous graft of mouse EL-4 T lymphoma, which expresses GD2 antigen, in mice of strain C57BL/6 (Zhang H, Zhang S, Cheung N K, Ragupathi G, Livingston P O. Antibodies against GD2 ganglioside can eradicate syngenic cancer micrometastases. Cancer Res. 1998, 58: 2844-9). These EL4 cells also express O-acetylated GD2 antigen. Twenty-four mice bred in an animal house, approved at A1 grade, were administered with a subcutaneous injection of $20\times10^4$ EL-4 cells suspended in PBS, at the age of 12 weeks. Two batches of 12 mice were constituted. The batch A mice were administered with 70 μg of mAb 8B6 as a solution in 200 μL of PBS buffer solution i.v., at 3 day intervals starting the first day after the injection of the EL4 cells and until the 21$^{st}$ day. The batch B mice were administered, according to the same procedure, only with 200 μL PBS solution. The volume of the tumors was then measured at two-day intervals. The tumor volume was assessed by using the following formula: volume (mm$^3$)=length (mm)×width$^2$ (mm)×0.5 (Zeng G, Li D D, Gao L, Birkle S, Bieberich E, Tokuda A, Yu R K; Alteration of ganglioside composition by stable transfection with antisense vectors against GD3-synthase gene expression. Biochemistry 1999 38: 8762-9). The mice showing a volume >3,000 mm$^3$ are sacrificed.

Figure 1:
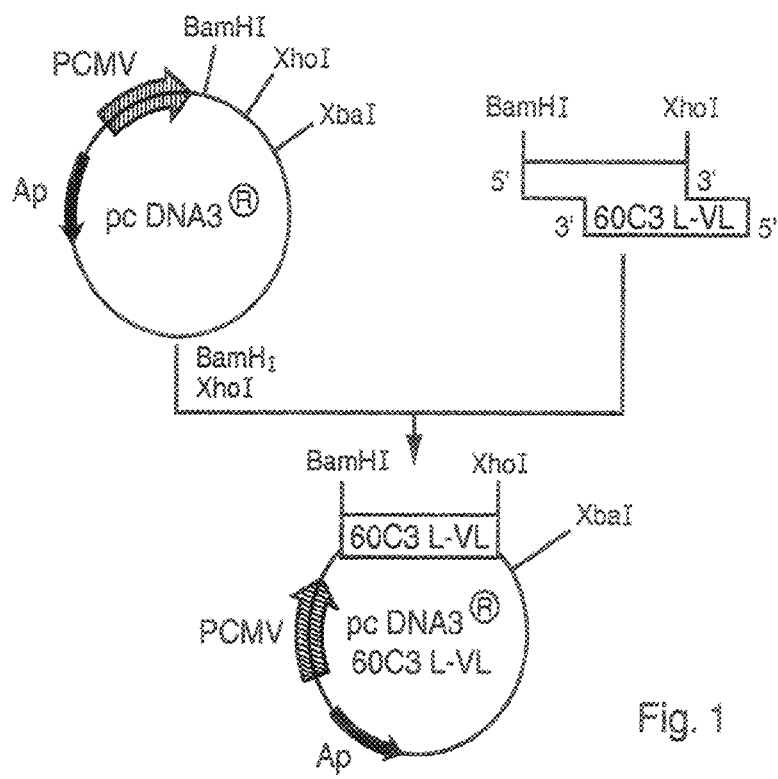
FIG. 1 illustrates the construction of the plasmid, pcDNA3®60C3 L-VL.
Figure 2:
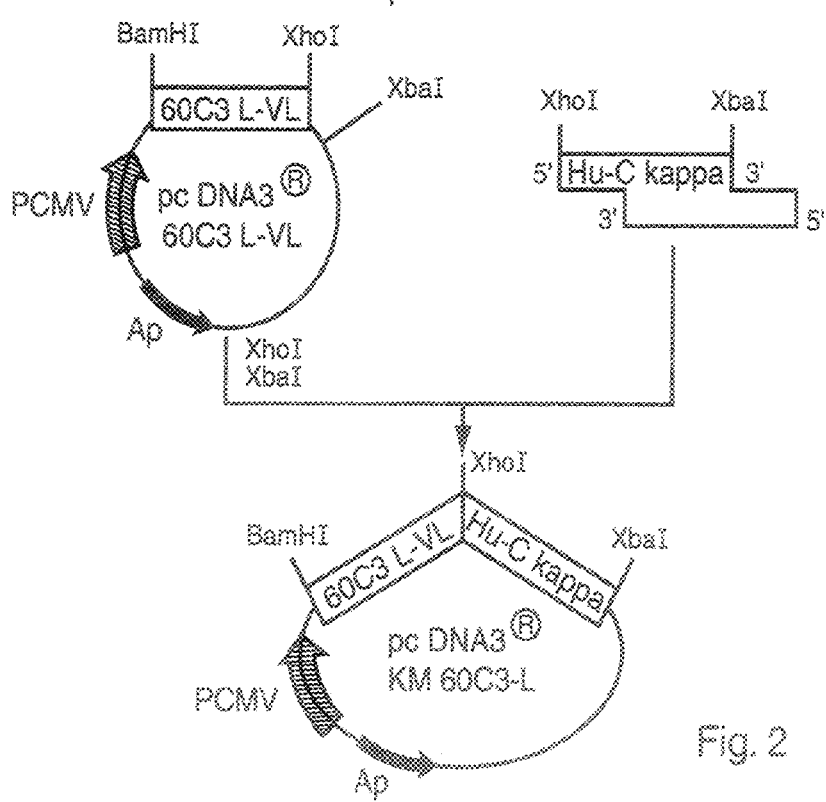
FIG. 2 illustrates the construction of the plasmid, pcDNA3®60C3 L.
Figure 6:
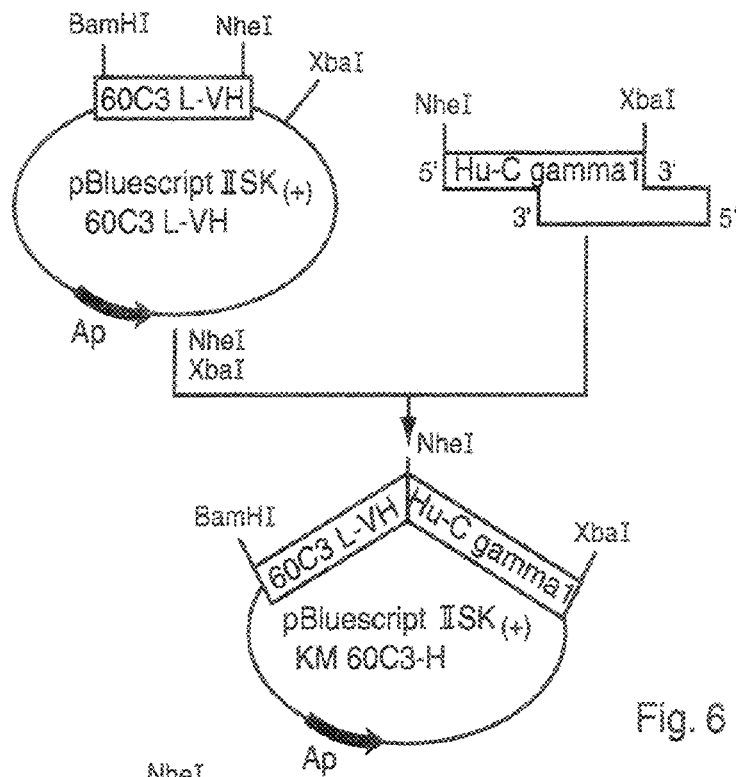
FIG. 6 illustrates the construction of the plasmid, pBluescript® II SK (+) KM60C3-H.
Figure 7:
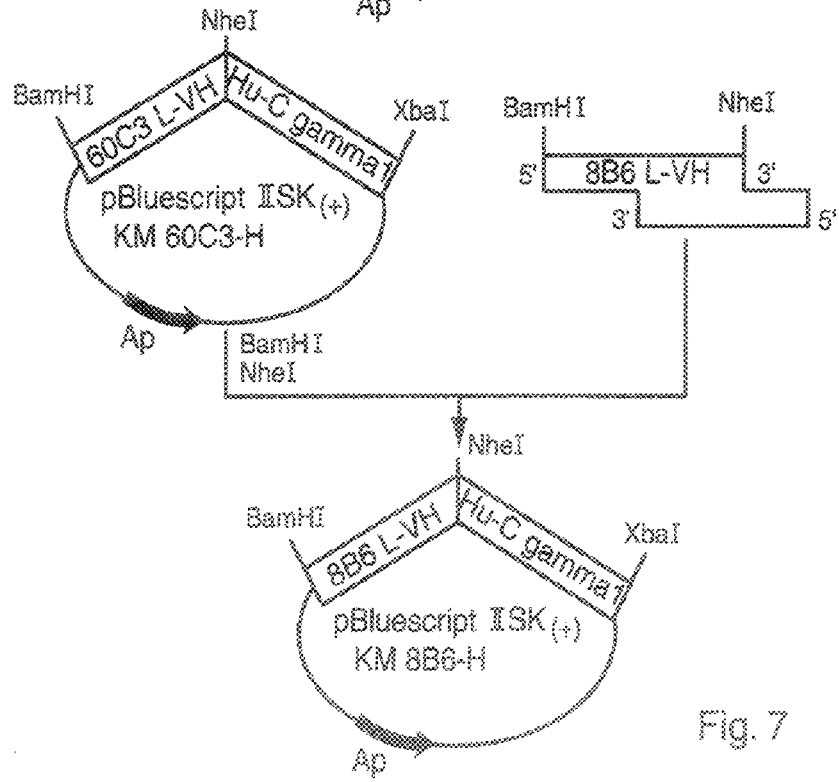
FIG. 7 illustrates the construction of the plasmid, pBluescript® II SK (+) KM8B6-H.
Figure 8:
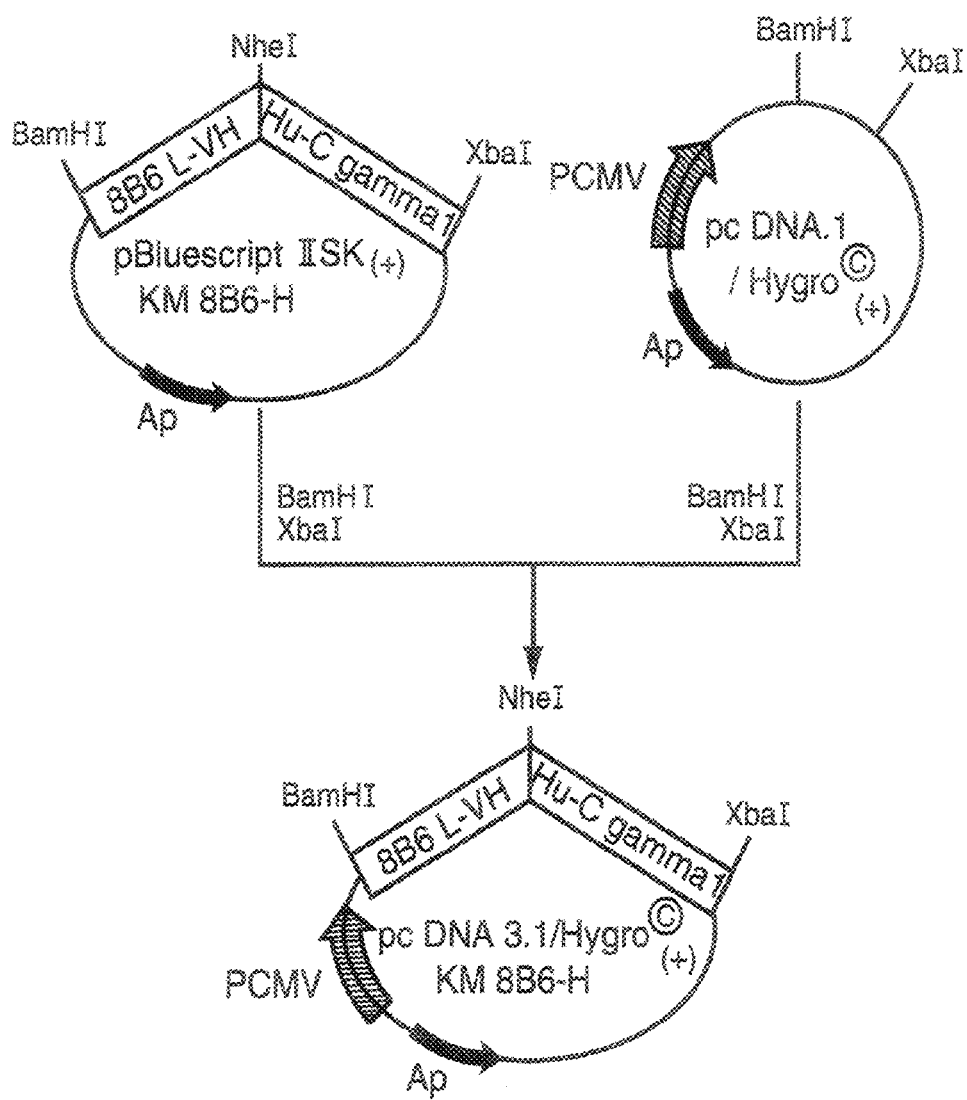
FIG. 8 illustrates the construction of the plasmid, pcDNA3.1/Hygro© (+) KM8B6-H.
Figure 10:
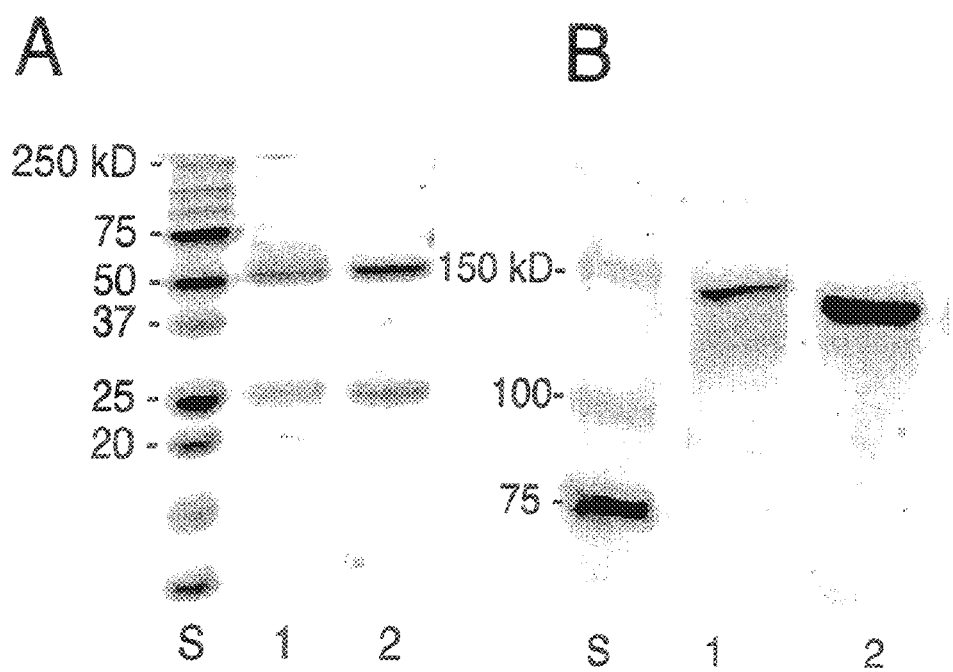
FIG. 10 illustrates SDS-PAGE analysis of the purified anti-O-acetylated GD2 artificially modified antibody, KM8B6. The analysis was carried out under reducing conditions (left-hand side) and under non-reducing conditions (right-hand side). From left to right, molecular weight marker, KM8B6, IgG3 8B6 (reducing conditions), high molecular weight marker, KM8B6, and IgG3 8B6 (non-reducing conditions).
Figure 11:
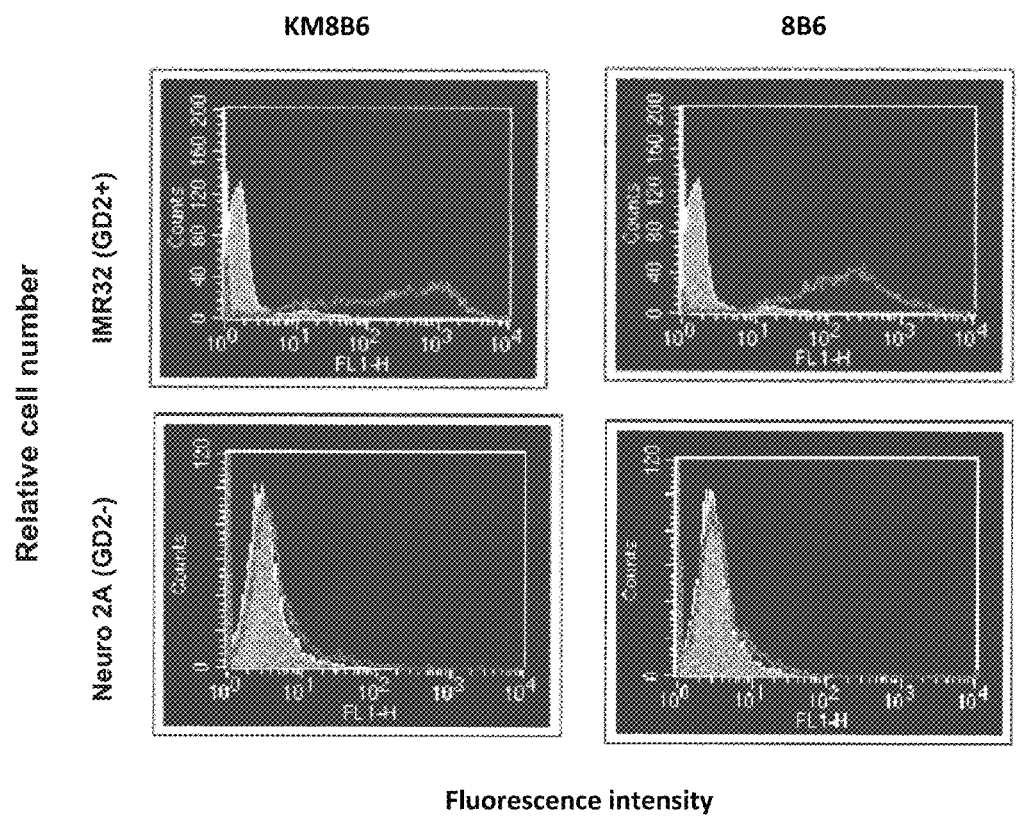
FIG. 11 is a graph illustrating the reactivity of 8B6 antibody and KM8B6 antibody on IMR-32 and NeuroA cells, with or without O-acetylated GD2 antigens, respectively, as measured by immunofluorescence, with the ordinate showing the number of cells detected and the abscissa showing the fluorescence intensity. The blue plot corresponds to the reactivity of the reference and the red plot corresponds to the reactivity of the products.
Figure 12:
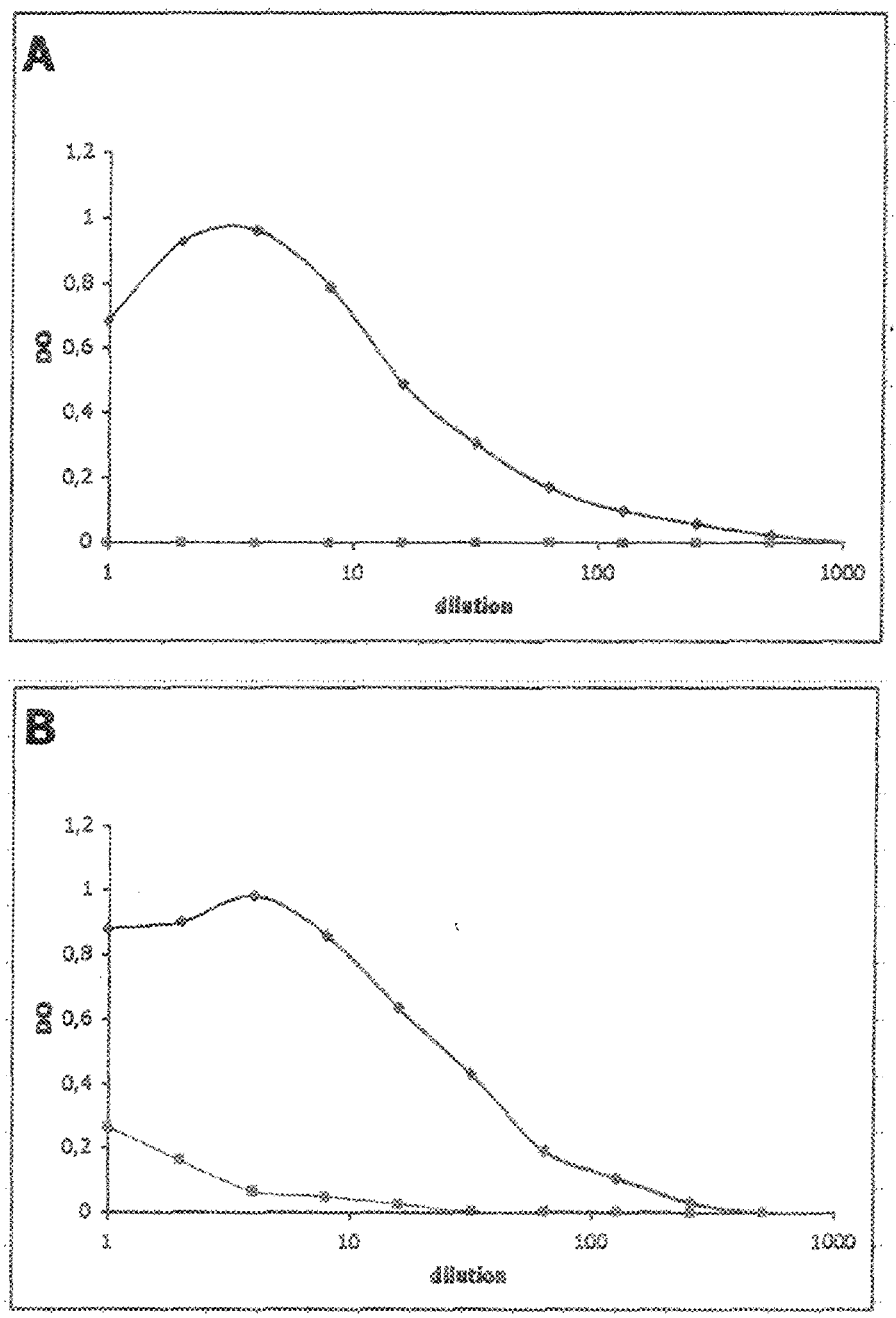
FIG. 12 is a graph illustrating the reactivity of 8B6 and KM8B6 antibodies tested by ELISA assay on IMR-32 and NeuroA cells.
Figure 13:
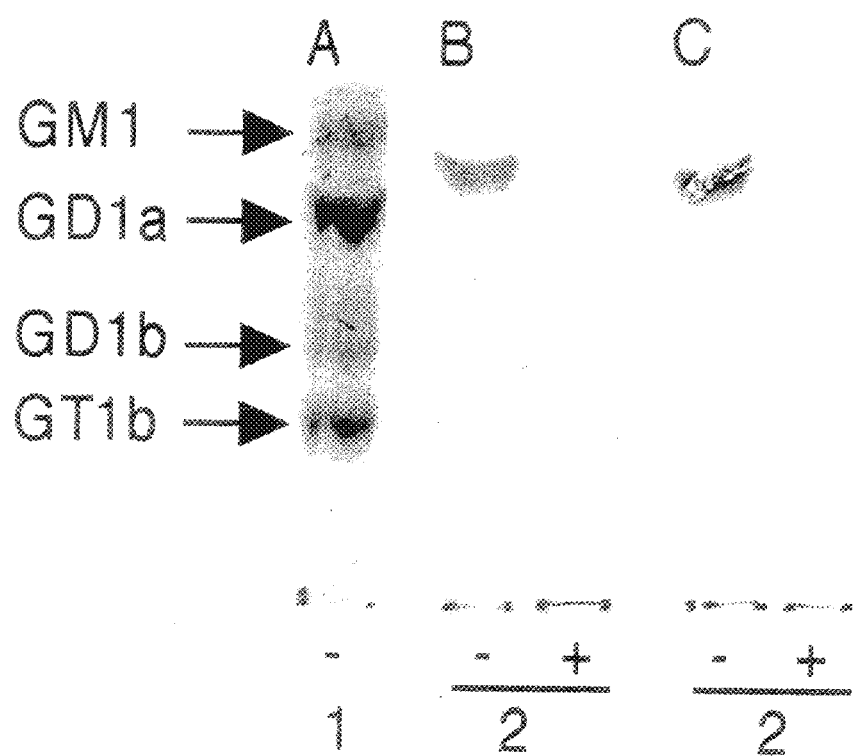
FIG. 13 shows the immunostaining profile obtained with the KM8B6 antibody from rat brain gangliosides separated by silica thin layer chromatography. Band A resorcinol staining of the migrations of various rat brain gangliosides.
Figure 14:
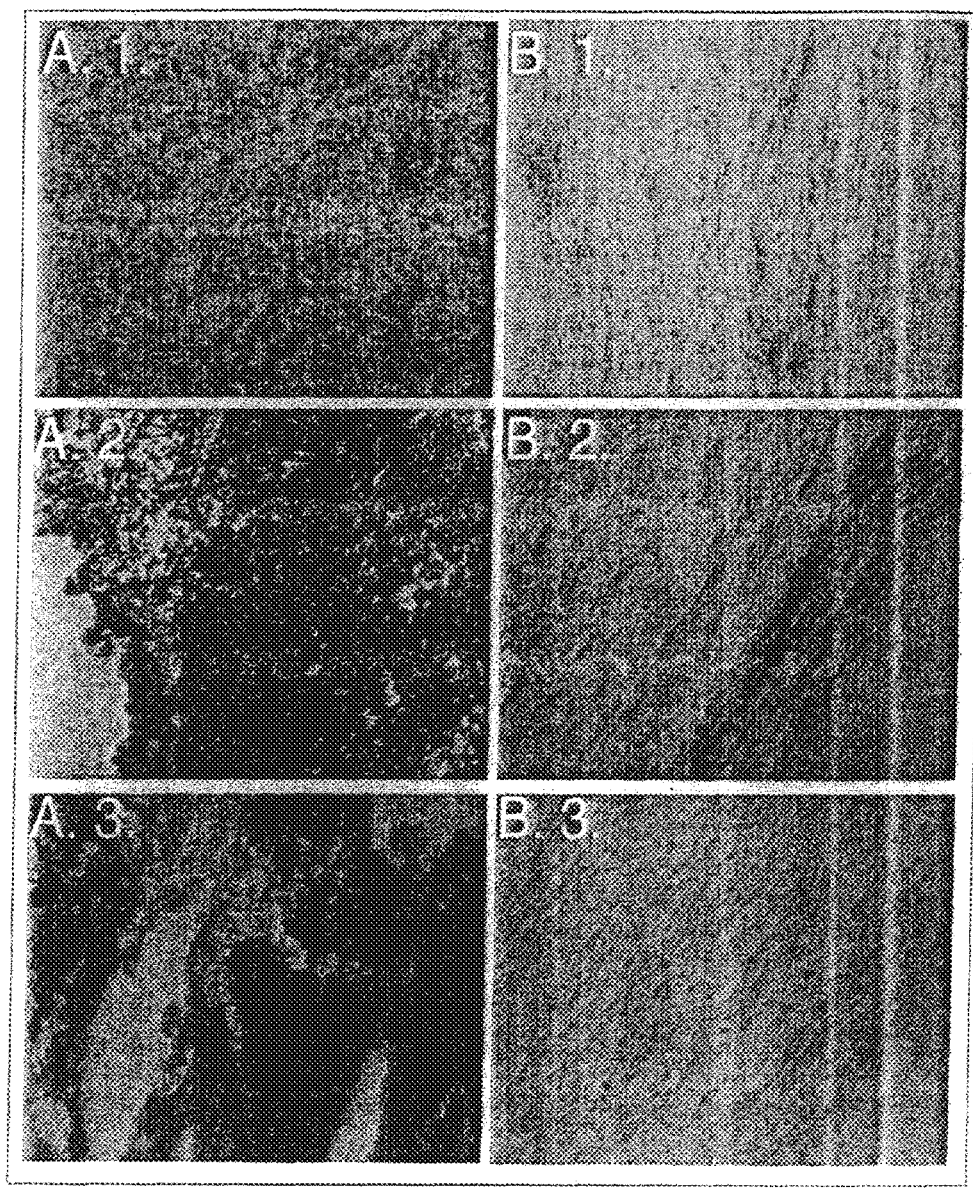
FIG. 14 shows the results of the immuno-histochemical assay of neuroblastoma cells and human nerve fibers.
Figure 16:
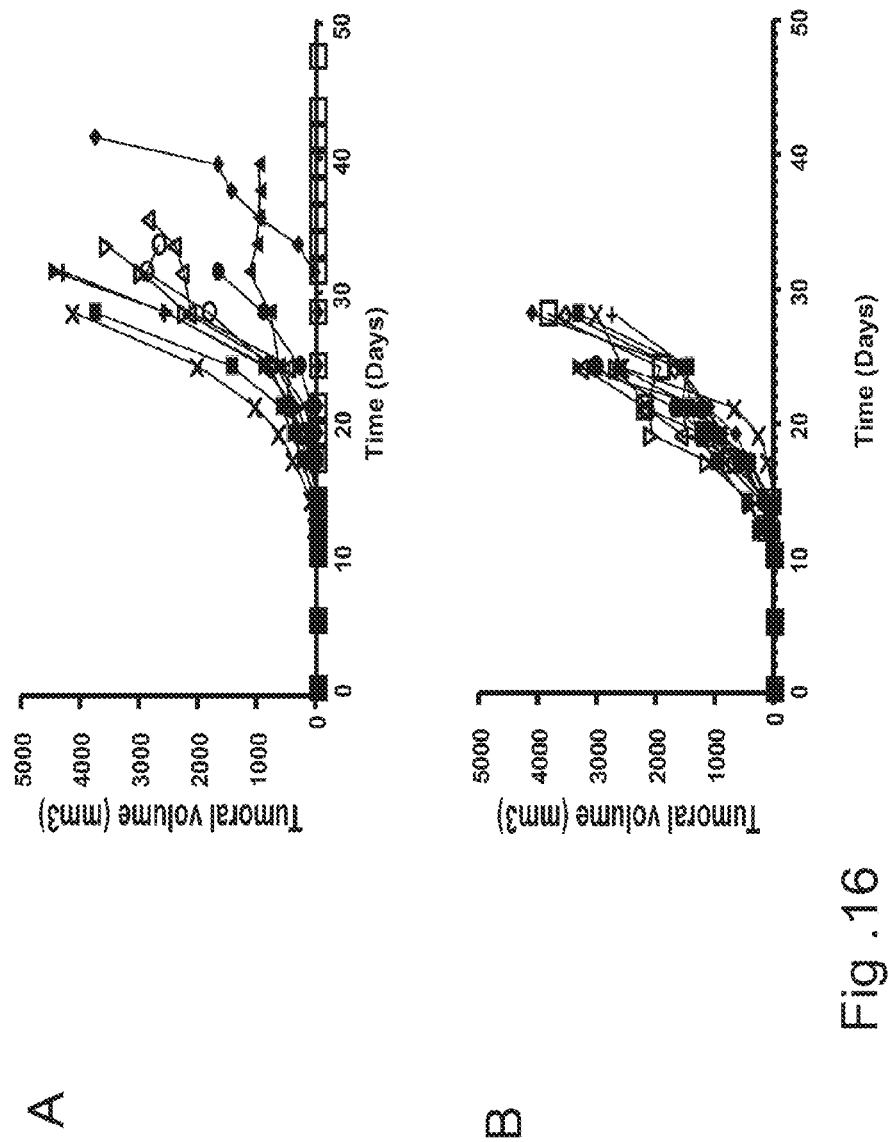
FIG. 16 shows the results of the in vivo study in mice of the antitumor effect of 8B6 mAb against murine EL4 thymoma which expressing O-acetylated GD2 antigen.

The results obtained are shown in FIG. 16. Batch B administered with PBS i.v., corresponds to the non-treated control batch (FIG. 16, plate B). The tumors begin to be detectable 10 days after inoculation and show subsequently an exponential growth. Twenty days after inoculation, all the mice but two have a tumor of more than 1000 mm$^3$. All the mice were sacrificed before day 30 according to animal experiment regulations because their tumor was larger than 3000 mm$^3$. In batch A mice, treated with 8B6 antibody (FIG. 16, plate A), a delay in the development of tumors is observed. Further, the tumor growth is slowed down in mice administered with this antibody. Twenty days after the inoculation, none of the treated mice has a tumor of more than 1000 mm$^3$. After 30 days, 58% of the mice treated with 8B6 mAb are surviving whereas all the non-treated mice are dead. After 40 days, 25% of the mice treated are still alive and after day 50, 8% of the mice are still alive and do not display palpable tumors and are regarded as cured.

Production of O-Acetyl-GD2 Chimeric Antigen Constructs (CARs)

1. Generation of Specific O-Acetyl-GD2 Chimeric Antigen Receptor Constructs.

CARs contain the 8B6 anti-O-Acetyl-GD2 single chain antibody that has been previously described (Cerato et al, hybridoma 1997). ScFv (8B6) was assembled in the orientation VH-linker-VL, with the synthetic (G4S)3 sequence serving as a flexible linker. The ScFv was linked to a flexible spacer derived from human engineered IgG1 Fc region from pFUSE-hIgG1e3-Fc1 plasmid (Invivogen, San Diego, USA). Substitution into human IgG1 of IgG2 residues at positions 233-236 and IgG4 residues at positions 327, 330 and 331 greatly reduced ADCC and CDC (Armour K L et al 1999 and Shields R L et al 2001). In 8B6-28Z CAR, the ScFv and the flexible spacer were linked to the CD28 transmembrane and intracellular domains (residues 151-220) and CD3 zeta intracellular domain (residues 52-164).

8B6-28 CAR is identical to 8B6-28Z CAR extracellular domain but preserves only the CD28 three first cytoplasmic amino acids after the transmembrane domain (residues 179-181) and lacks the CD3 zeta cytoplasmic domain. The O-Acetyl-GD2 CAR constructs were synthetized by PCR (GeneCust Europe, Dudelange, Luxembourg) and cloned into a retroviral pMX vector [Onishi M, Kinoshita S, Morikawa Y, et al. Exp Hematol. 1996; 24:324-329].

2. Cells Lines.

For retroviral production we used helper-virus-free Phoenix-Ampho packaging cells (G. P., Nolan, Standford, Calif.). Phoenix cell lines were maintained in high-glucose (4.5 g/liter) Dulbecco's modified Eagle's medium (DMEM) (Gibco, Cergy, France) supplemented with 10% FBS (Gibco) and 2 mM L-glutamine (Sigma Aldrich). The NK-92 human NK cell line (from ATCC) was grown in RPMI 1640 culture medium (Gibco, Cergy) supplemented with 10% FBS, 2 mM L-glutamine, penicillin (100 IU/ml), streptomycin (0.1 μg/ml) (Gibco) and 100 UI/ml (Proleukin, Novartis Pharmaceuticals Corporation).

3. In Vitro Expansion of γδ T Cells.

Whole blood samples from healthy donors were taken into EDTA. PBMCs were isolated by Ficoll gradient centrifugation from whole blood and frozen in liquid nitrogen until use. All cell cultures were performed in RPMI 1640 culture medium supplemented with 8% human serum. For γδ T cell expansion, total PBMCs ($1.5\times10^6$/ml) were stimulated with 5 μM Zoledronate (Zometa; Novartis Pharmaceuticals Corporation) in 24-well plates and cultured at 37° C. in 5% CO2. At days 3, cell cultures were supplemented with 100 IU IL2/ml. At day 14, γδ T cells cultures were examined by flow cytometry for γδ T cell expansion and purity. γδ T cells represented at least 90% of the cells in the culture. Then γδ T cells cultures were amplified with PHA/feeders/IL2 and transduced 3 days after the stimulation.

4. Production of Amphotropic Retroviral Vectors and Transduction of NK-92 Cells or γδ T Cells.

Transient retroviral supernatants were produced by transfection of Phoenix-Ampho packaging cells. Two million Phoenix-Ampho cells were seeded in 10-cm-diameter dishes 24 h prior to transfection. Transfection was performed with 15 μg pMX/O-Acetyl-GD2 CAR plasmid DNA using Calcium Phosphate transfection kit (Invitrogen, Carisbad, USA). The medium (10 ml) was replaced 6 h after transfection. The conditioned medium was collected 48 h post-transfection, filtered through 0.45-μm pore-size filters and kept at –80° C. until use. NK-92 cell line or γδ T cells were resuspended in complete RPMI 1640 culture medium, seeded at $1\times10^6$ cells in 1 ml per well into 6-well plates and exposed to 2×2 ml of retroviral supernatant by spinoculation (2400 g, 1.5 h, 32° C.) in the presence of 4 μg/ml polybrene (Sigma, St Quentin Fallavier, France). The culture medium was changed 24 h post-infection. Mock (non-transduced) controls were performed in parallel, by which the supernatant of untransfected packaging cells was added to the NK-92 cell line. Transduction levels were assessed 4 days later by staining the CAR-transduced NK-92 cell lines or γδ T cells with a PE-conjugated Goat F(ab')2 polyclonal secondary antibody to human IgG-Fc, pre-absorbed) (abcam, Cambridge, UK).

5. FACS Sorting of Transduced NK-92 Cell Lines

After transduction, NK-92$^{8B6\text{-}CD28Z}$ and NK-92$^{8B6\text{-}CD28}$ cells were stained with a PE-conjugated Goat F(ab')2 polyclonal secondary antibody to human IgG-Fc and Facs-sorting was performed on BD FACS ARIA sorter (BD Biosciences).

6. Cytotoxicity Assay

Cytotoxic activity was assessed using a standard $^{51}$Cr release assay. Target cells were labeled overnight with $^{51}$Cr (40 μCi/ml) at 37° C., washed four times with culture medium, and then plated at the indicated effector-to-target cell ratio in a 96-well flat-bottom plate. After a 4 h incubation at 37° C., 25 μl of supernatant were removed from each well, mixed with 100 μl scintillation fluid, and $^{51}$Cr activity was counted in a scintillation counter. Each test was performed in triplicate. The results are expressed as the percentage of lysis, which is calculated according to the following equation: (experimental release-spontaneous release)/(maximal release-spontaneous release)×100, where experimental release represents the mean counts per minute (cpm) for the target cells in the presence of effector cells, spontaneous release represents the mean cpm for target cells incubated without effector cells, and maximal release represents the mean cpm for target cells incubated with 1% Triton x 100.

Results

1. Specific O-Acetyl-GD2 Chimeric Antigen Receptor Constructs.

O-Acetyl-GD2 specific CARs were derived from the heavy and light chain variable domains of the murine monoclonal IgG3 8B6. As illustrated by FIG. 17, VH-linker-VL (ScFv) was connected to a flexible spacer derived from human engineered IgG1 Fc region to reduce binding to IgG Fc receptors (FcεR) and the complement factors. Hombach et al has previously revealed that CARs with Fc spacer domain from IgG1 bind to FcεR, thereby unintentionally activating innate immune cells, including monocytes and natural killer (NK) cells. CARs expressing T cells, on the other hand, are likewise activated by FcεR binding resulting in cytokine secretion and lysis of monocytes and NK cells independently of the CARs specificity. As illustrated by FIG. 17, in 8B6-28Z CAR, the ScFv and the flexible spacer were linked to the CD28 transmembrane and intracellular domains (residues 151-220) and CD3 zeta intracellular domain (residues 52-164). The 8B6-28 CAR preserves only the CD28 three first cytoplasmic amino acids after the transmembrane domain (residues 179-181) and lacks the CD3 zeta cytoplasmic domain.

2. Generation of CARs of CARs 8B6-28 and 8B6-28Z Transduced NK-92 Cell Line.

Amphotropic retroviral vectors particules were produced by transfection of Phoenix-Ampho packaging cells and used for transduction of the human natural killer cell line NK-92 (Gong, J H, 1994 p652). Four days after transduction 36% and 32% of the NK-92 CAR 8B6-28Z and NK-92 CAR 8B6-28Z cells expressed the CAR 8B6-28Z or the CAR 8B6-28 respectively as assessed by flow cytometry (FIG. 18). After FACS sorting, expression of both transgenes was shown to remain stable during the 3 months of follow-up (not shown).

3. Cytotoxicity Activity by NK-92 CAR 8B6-28Z and NK-92 CAR 8B6-28Z

The cytotoxicity activity of CARs anti-O-acetyl-GD2 expressing NK-92 cells were evaluated against the LAN-5 human neuroblastoma cell line and ten primary human glioblastoma cultures. None of these tumor cells were lysed by NK-92 NT or the NK-92$^{CAR\ 8B6\text{-}28}$. This confirms that the later is unable to transduce cellular signal. In contrast, the neuroblastoma cell line LAN-5 was efficiently lysed by NK-92$^{CAR\ 8B6\text{-}28Z}$. In addition, all primary human glioblastoma cultures were also lysed at different levels. The U87 glioblastoma cell line which 28Z O-acetyl-GD2 negative was not lysed by the NK-92 CAR 8B6-(Table I).

TABLE I

Cytotoxicity activity of non transduced (NT) NK-92, NK-92$^{CAR8B6\text{-}28}$ and NK-92$^{CAR8B6\text{-}28Z}$ cell lines. Cytotoxic activity was assessed using a standard $^{51}$Cr release assay at an E/T ratio of 10:1.

| | | O-acetyl-GD2 expression | Percent specific lysis[a] | | |
|---|---|---|---|---|---|
| | | | NK-92$^{NT}$ | NK-92$^{AR\ 8B6\text{-}28}$ | NK-92$^{CAR\ 8B6\text{-}28Z}$ |
| | U87 (glioblastoma) | — | –3[b] | 4 | 3 |
| | LAN5 (neuroblastoma) | +(94%) | 1 | 2 | 51 |
| Primary GMB | #1 | +(92%) | 0 | 1 | 6 |
| | #2 | +(86%) | 1 | 1 | 41 |
| | #3 | +(53%) | 0 | 0 | 8 |
| | #4 | +(83%) | 2 | 3 | 15 |
| | #5 | +(69%) | –1 | 4 | 41 |
| | #6 | +(76%) | 5 | 9 | 17 |
| | #7 | +(91%) | 4 | –4 | 13 |

TABLE I-continued

Cytotoxicity activity of non transduced (NT) NK-92, NK-92$^{CAR8B6-28}$ and NK-92$^{CAR8B6-28Z}$ cell lines. Cytotoxic activity was assessed using a standard $^{51}$Cr release assay at an E/T ratio of 10:1.

| | O-acetyl-GD2 expression | Percent specific lysis$^a$ | | |
|---|---|---|---|---|
| | | NK-92$^{NT}$ | NK-92$^{AR\ 8B6-28}$ | NK-92$^{CAR\ 8B6-28Z}$ |
| #8 | +(17%) | −1 | 3 | 18 |
| #9 | +(61%) | 0 | 4 | 9 |
| #10 | +(50%) | 1 | 2 | 16 |

$^a$ = E:T ratio = 10:1
$^b$ = mean of two independent experiments

4. Generation of CARs 8B6-28 and 8B6-28Z Transduced Human γδ T Cells.

Human γδ T cells selected and amplified with Zoledronic acid (Zoledronate, Novartis) were stimulated and transduced three days after the non specific stimulation. Transduction levels, assessed by staining the CAR-transduced γδ T cells with a PE-conjugated Goat F(ab')2 polyclonal anti-human IgG-Fc, were 10% for CAR 8B6-28Z and 14% for the CAR 8B6-28 respectively as assessed by flow cytometry (FIG. 19).

The invention claimed is:

1. A method for the treatment of cancers expressing the O-acetylated form of GD2 ganglioside selected from the group consisting of neuroblastomas, lymphomas, melanomas, glioblastomas and small cell lung cancers, said method comprising administering to a patient in need thereof an antibody or a fragment thereof that specifically binds to O-acetylated GD2 ganglioside and which is coupled to a biological toxic molecule (BTM), wherein said antibody or a fragment thereof has the complementarity-determining regions of the H chain variable region comprising amino acid sequences represented in SEQ ID NO:2, SEQ ID NO:3 and SEQ ID NO:4 and has the complementarity-determining regions of the L chain variable region comprising amino acid sequences represented in SEQ ID NO:6, SEQ ID NO:7 and SEQ ID NO:8, wherein said antibody has an affinity of at least ten times lower for the non O-acetylated form of GD2 ganglioside and wherein an effective amount of said antibody or a fragment thereof coupled to a biological toxic molecule (BTM) provides cytotoxic activity against said cancer cells.

2. The method in accordance to claim 1, wherein said antibody fragment is in the form of single chain fragments of heavy and light chain variable regions (scFv).

3. The method in accordance with claim 1, wherein the coupled antibody or a fragment thereof and BTM are covalently linked to form a chimeric antigen receptor (CAR).

4. The method in accordance with claim 3, wherein the CAR comprises an ectodomain, a transmembrane domain and an endodomain.

5. The method in accordance with claim 4, wherein:
i) the ectodomain comprises an O-acetylated GD2 ganglioside antigen binding domain having the CDRs as defined by the sequences of SEQ ID NO:2, 3, 4, 6, 7 and 8 and an extracellular hinge domain,
ii) the transmembrane domain comprises a T cell receptor transmembrane domain, and
iii) the endodomain comprises a T cell receptor signaling domain.

6. The method in accordance with claim 5, wherein the extracellular hinge domain is derived from IgG1, IgG2, IgG3 or IgG4 hinge domain.

7. The method in accordance with claim 5, wherein the T cell receptor transmembrane domain comprises part or all of the transmembrane domain of TCR Zeta chain (CD3ζ), CD28, OX40/CD134, 4-1BB/CD137/TNFRSF9, FcεRIγ, ICOS/CD278, ILRB/CD122, IL-2RG/CD132, or CD40.

8. The method in accordance with claim 5, wherein the T cell receptor signaling domain comprises part or all of the signaling domain containing the signaling motifs of TCR Zeta chain (CD3ζ), CD28, OX40/CD134, 4-1BB/CD137/TNFRSF9, FcεRIγ, ICOS/CD278, ILRB/CD122, IL-2RG/CD132, or CD40, said signaling motifs allowing intracellular signaling.

* * * * *